US012685866B2

(12) United States Patent
Single

(10) Patent No.: US 12,685,866 B2
(45) Date of Patent: Jul. 21, 2026

(54) FEEDBACK CONTROL OF NEUROMODULATION DEVICE

(71) Applicant: Saluda Medical Pty Limited, Artarmon (AU)

(72) Inventor: Peter Scott Vallack Single, Artarmon (AU)

(73) Assignee: Saluda Medical Pty Limited, Macquarie Park (AU)

( * ) Notice: Subject to any disclaimer, the term of this patent is extended or adjusted under 35 U.S.C. 154(b) by 257 days.

(21) Appl. No.: 18/575,520

(22) PCT Filed: Jun. 28, 2022

(86) PCT No.: PCT/AU2022/050660
§ 371 (c)(1),
(2) Date: Dec. 29, 2023

(87) PCT Pub. No.: WO2023/272343
PCT Pub. Date: Jan. 5, 2023

(65) Prior Publication Data
US 2025/0001180 A1 Jan. 2, 2025

(30) Foreign Application Priority Data
Jul. 1, 2021 (AU) ................................. 2021902010

(51) Int. Cl.
*A61N 1/36* (2006.01)

(52) U.S. Cl.
CPC ....... *A61N 1/36139* (2013.01); *A61N 1/3615* (2013.01)

(58) Field of Classification Search
CPC ............ A61N 1/36062; A61N 1/36071; A61N 1/36135; A61N 1/36139
See application file for complete search history.

(56) References Cited

U.S. PATENT DOCUMENTS 5,913,882 A    6/1999   King et al.
7,295,881 B2   11/2007  Cohen et al.
(Continued)

FOREIGN PATENT DOCUMENTS

DE        19758110       7/2004
WO     WO2006055849      5/2006
(Continued)

OTHER PUBLICATIONS

Gorman et al., Neural Recordings For Feedback Control of Spinal Cord Stimulation: Reduction of Paresthesia Variability, 2013, presented at the International Neuromodulation Society 11th World Congress, Berlin, Germany, 2 pgs.
(Continued)

*Primary Examiner* — George R Evanisko
(74) *Attorney, Agent, or Firm* — Barnes & Thornburg LLP

(57) ABSTRACT

There is provided a method of controlling a neural stimulus. The neural stimulus is defined by at least one stimulus parameter. The method comprises generating a neural stimulus for application to a neural tissue of a patient in accordance with a stimulus parameter, at a first stimulus intensity level, and measuring a response of the neural tissue, the response being evoked by the neural stimulus. The method further comprises determining a second stimulus intensity level, based on an activation plot intercept point, the first stimulus intensity level, the measured response of the neural tissue and a target recruitment level, and adjusting the at least one stimulus parameter to the second stimulus intensity level.

15 Claims, 16 Drawing Sheets

(56)                  References Cited

U.S. PATENT DOCUMENTS

| | | | |
|---|---|---|---|
| 7,450,992 | B1 | 11/2008 | Cameron |
| 8,762,065 | B2 | 6/2014 | Dilorenzo |
| 9,205,263 | B2 | 12/2015 | King et al. |
| 9,302,112 | B2 | 4/2016 | Bornzin et al. |
| 9,381,356 | B2 | 7/2016 | Parker et al. |
| 9,387,325 | B1 | 7/2016 | Min et al. |
| 9,492,667 | B1 | 11/2016 | Kent et al. |
| 9,511,231 | B1 | 12/2016 | Kent et al. |
| 9,737,719 | B2 | 8/2017 | Skelton et al. |
| 9,907,960 | B2 | 3/2018 | Lian et al. |
| 9,950,171 | B2 | 4/2018 | Johanek et al. |
| 10,471,264 | B2 | 11/2019 | Bourget et al. |
| 10,500,399 | B2 * | 12/2019 | Single .............. A61N 1/36062 |
| 10,842,996 | B2 | 11/2020 | Baru et al. |
| 11,090,493 | B2 | 8/2021 | Hou et al. |
| 11,259,732 | B2 | 3/2022 | Parramon et al. |
| 11,273,311 | B2 | 3/2022 | Su |
| 11,642,531 | B2 | 5/2023 | Li et al. |
| 11,684,774 | B2 | 6/2023 | Crosby et al. |
| 11,786,725 | B2 | 10/2023 | Beck et al. |
| 2003/0153959 | A1 | 8/2003 | Thacker et al. |
| 2013/0165998 | A1 | 6/2013 | Libbus et al. |
| 2014/0277282 | A1 | 9/2014 | Jaax |
| 2019/0192855 | A1 | 6/2019 | Bharmi et al. |
| 2021/0345950 | A1 | 11/2021 | Annoni et al. |
| 2022/0054843 | A1 | 2/2022 | Carcieri |
| 2022/0218996 | A1 | 7/2022 | Dinsmoor et al. |
| 2022/0323766 | A1 | 10/2022 | Hughes et al. |
| 2023/0067424 | A1 | 3/2023 | Crosby et al. |
| 2023/0241397 | A1 | 8/2023 | Parker et al. |
| 2023/0321438 | A1 | 10/2023 | Sachs et al. |
| 2023/0321439 | A1 | 10/2023 | Sachs et al. |

FOREIGN PATENT DOCUMENTS

| | | |
|---|---|---|
| WO | WO2006017277 | 6/2006 |
| WO | WO2007064936 | 6/2007 |
| WO | WO2009015005 | 1/2009 |
| WO | WO2009046764 | 4/2009 |
| WO | WO2009051965 | 4/2009 |
| WO | WO2010080222 | 7/2010 |
| WO | WO2010088417 | 8/2010 |
| WO | WO2011112773 | 12/2011 |
| WO | WO2011159545 | 12/2011 |
| WO | WO2012155187 | 11/2012 |
| WO | WO2012155188 | 11/2012 |
| WO | WO2012155189 | 11/2012 |
| WO | WO2013063111 | 5/2013 |
| WO | WO2015031136 | 3/2015 |
| WO | WO2016057212 | 4/2016 |
| WO | WO2016057544 | 4/2016 |
| WO | WO2016090436 | 6/2016 |
| WO | WO2017173493 | 10/2017 |
| WO | WO2017184238 | 10/2017 |
| WO | WO2018063912 | 4/2018 |
| WO | WO2018080753 | 5/2018 |
| WO | WO2018089981 | 5/2018 |
| WO | WO2018152064 | 8/2018 |
| WO | WO2019027578 | 2/2019 |
| WO | WO2019067059 | 4/2019 |
| WO | WO2019070406 | 4/2019 |
| WO | WO2019136072 | 7/2019 |
| WO | WO2019177798 | 9/2019 |
| WO | WO2019190710 | 10/2019 |
| WO | WO2019204884 | 10/2019 |
| WO | WO2019190679 | 12/2019 |
| WO | WO2019246579 | 12/2019 |
| WO | WO2019246582 | 12/2019 |
| WO | WO2020047152 | 3/2020 |
| WO | WO2020206152 | 10/2020 |
| WO | WO2020243096 | 12/2020 |
| WO | WO2020251899 | 12/2020 |
| WO | WO2020257705 | 12/2020 |
| WO | WO2021030152 | 2/2021 |
| WO | WO2021080834 | 4/2021 |
| WO | WO2021080835 | 4/2021 |
| WO | WO2021080836 | 4/2021 |
| WO | WO2021126431 | 6/2021 |
| WO | WO2021126432 | 6/2021 |
| WO | WO2021126587 | 6/2021 |
| WO | WO2021126588 | 6/2021 |
| WO | WO2021162794 | 8/2021 |
| WO | WO2021162795 | 8/2021 |
| WO | WO2021178265 | 9/2021 |
| WO | WO2021211170 | 10/2021 |
| WO | WO2021252257 | 12/2021 |
| WO | WO2021262861 | 12/2021 |
| WO | WO2022010677 | 1/2022 |
| WO | WO2021255473 | 2/2022 |
| WO | WO2022040754 | 3/2022 |
| WO | WO2022040757 | 3/2022 |
| WO | WO2022040758 | 3/2022 |
| WO | WO2022072256 | 4/2022 |
| WO | WO2022098837 | 5/2022 |
| WO | WO2022104387 | 5/2022 |
| WO | WO2022155032 | 7/2022 |
| WO | WO2022155339 | 7/2022 |
| WO | WO2022170388 | 8/2022 |
| WO | WO2022183161 | 9/2022 |
| WO | WO2022183189 | 9/2022 |
| WO | WO2022225879 | 10/2022 |
| WO | WO2022261012 | 12/2022 |

OTHER PUBLICATIONS

International Search Report and Written Opinion in PCT/AU2022/050660, 16 pages.

Kent, Characterization of Evoked Potentials During Deep Brain Stimulation in the Thalamus, 2013, Dissertation, Duke University. Retrieved from https://hdl.handle.net/10161/8195, https://dukespace.lib.duke.edu/dspace/handle/10161/8195.

Laird-Wah, Improving Spinal Cord Stimulation: Model-Based Approaches to Evoked Response Telemetry, UNSW Thesis, Aug. 2015, 279 pgs.

Second Written Opinion in in PCT/AU2022/050660, 5 pages.

Parker et al., Closing the Loop in Neuromodulation Therapies: Spinal Cord Evoked Compound Action Potentials During Stimulation for Pain Management (230), 2011, In 15th Annual Meeting, North American Neuromodulation Society (p. 48). Presented at the North American Neuromodulation Society, Las Vegas, Nevada.

* cited by examiner

1500

Start

Derive activation data sets

1502

Determine activation plots

1504

Adjust activation plot(s)

1506

Communicate activation profile intercept point

1508

Method 1200

1510

FEEDBACK CONTROL OF NEUROMODULATION DEVICE

CROSS-REFERENCE TO RELATED APPLICATIONS

The present is a 371 national stage Application from PCT/AU2022/050660, filed Jun. 28, 2022, which claims priority from Australian Provisional Patent Application No 2021902010 filed on 1 Jul. 2021, the contents of each of which are incorporated herein by reference in their entirety.

TECHNICAL FIELD

The present invention relates to controlling a neural stimulus, and in particular relates to measurement of an evoked compound action potential by using one or more electrodes implanted near a neural pathway, in order to provide feedback to control subsequently applied stimuli.

BACKGROUND

There is a range of situations in which it is desirable to apply neural stimuli in order to give rise to a compound action potential (CAP) in a tissue. For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. The electrode array applies an electrical pulse to the dorsal column, which causes the depolarisation of neurons, and generation of propagating action potentials. This stimulates the nerve fibres and, as a result, inhibits the transmission of pain from that segment in the spinal cord to the brain. The electrode array applies stimuli continuously to sustain the pain relief effects. Neuromodulation may also be used to stimulate efferent fibres, for example to induce motor functions.

In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form an electrically evoked compound action potential (ECAP). Accordingly, an ECAP is the sum of responses from a large number of single fibre action potentials. The ECAP recorded is the result of a large number of different fibres depolarising. The ECAP generated from the firing of a group of similar fibres is measured as a positive peak potential, then a negative peak, followed by a second positive peak. This is caused by the region of activation passing a recording electrode as the action potentials propagate along the individual fibres.

For effective and comfortable operation, it is desirable to maintain an electrical stimulus above a recruitment threshold (otherwise known as the perception threshold), below which the electrical stimulus will fail to recruit any neural response and the patient will be unable to perceive an effect. It is also desirable to maintain an electrical stimulus which is below a comfort threshold, above which uncomfortable or painful percepts arise due to increasing recruitment of Aδ fibres, which are thinly myelinated sensory nerve fibres associated with acute pain, cold and pressure sensation.

The stimuli can be delivered within a therapeutic range (above the recruitment threshold and below the comfort threshold) by adjusting the amplitude of applied stimulus based on a feedback signal. The feedback signal is based on a measured ECAP value, detected by an electrode connected to the nerve fibres upstream of the stimulating electrode. Based on the ECAP value, the amplitude of the applied stimulus can be adjusted to maintain the nerve stimulus within the therapeutic range. A method for achieving this is disclosed in U.S. Pat. No. 9,381,356 B2 by the present applicant, and U.S. Pat. No. 10,500,399 B2 by the present applicant, the contents of both of which are incorporated herein by reference.

The task of maintaining appropriate stimulus amplitude is made more difficult by electrode migration and/or postural changes of the implant recipient (patient), either of which can significantly alter the neural recruitment arising from a given stimulus, depending on whether the stimulus is applied before or after the change in electrode position or user posture. Postural changes alone can cause a comfortable and effective stimulus regime to become either ineffectual or painful. Furthermore, it is often desirable to maintain stimulation at, or close to, a target stimulation level, within a therapeutic range.

Accordingly, it is desirable to provide a neural stimulation device that can maintain stimulation at, or close to, a target stimulation level, even in the event of electrode movement and/or postural changes of the patient.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word 'comprise', or variations such as 'comprises' or 'comprising', will be understood to imply the inclusion of a stated element, integer or step, or group of elements, integers or steps, but not the exclusion of any other element, integer or step, or group of elements, integers or steps.

SUMMARY

In accordance with aspects of the present technology, there is provided a neural stimulation feedback loop controller which is configured to adjust an intensity level of a stimulus parameter to evoke a neural response that recruits a target number of neural fibres of a patient, even as the patient changes posture.

In accordance with one aspect of the present technology, there is provided a method of controlling a neural stimulus, the neural stimulus being defined by at least one stimulus parameter. The method comprises generating a neural stimulus for application to a neural tissue of a patient in accordance with a stimulus parameter, at a first stimulus intensity level, and measuring a response of the neural tissue, the response being evoked by the neural stimulus. The method further comprises determining a second stimulus intensity level, based on an activation plot intercept point, the first stimulus intensity level, the measured response of the neural tissue and a target recruitment level, and adjusting the at least one stimulus parameter to the second stimulus intensity level.

In one embodiment, the method further comprises determining a threshold stimulus intensity level, based on the activation plot intercept point, the first stimulus intensity level and the measured response of the neural tissue, wherein determining the second stimulus intensity level comprises determining the second stimulus intensity level based on the threshold stimulus intensity level and the target recruitment level.

In one embodiment, the activation plot intercept point indicates an intercept point for a plurality of activation plots associated with the neural tissue. In one embodiment, each activation plot of the plurality of activation plots is indicative of a relationship between the at least one stimulus parameter and an evoked response of the neural tissue, wherein each relationship comprises a monotonically increasing linear section, and the monotonically increasing linear section can be extrapolated on a Cartesian plane to produce an extrapolated linear section, and wherein the extrapolated linear section of each activation plot of the plurality of activation plots passes through the activation plot intercept point.

In one embodiment, the activation plot intercept point comprises an intercept stimulus intensity term and an intercept evoked response term.

In one embodiment, determining the threshold stimulus intensity level comprises determining a first term to be equal to the intercept evoked response term multiplied by the first stimulus intensity level, determining a second term to be equal to the intercept stimulus intensity term multiplied by the measured response of the neural tissue, determining a third term to be equal to the measured response of the neural tissue added to the intercept evoked response term, determining a fourth term to be equal to the first term added to the second term, and determining a threshold stimulus intensity level to be equal to the fourth term divided by the third term.

In one embodiment, determining the second stimulus intensity level comprises determining a multiplication of the threshold stimulus intensity level and the target recruitment level plus one. In one embodiment, determining the second stimulus intensity level comprises calculating an estimated recruitment level, and determining a difference between the estimated recruitment level and the target recruitment level.

In one embodiment, the method further comprises receiving configuration information indicative of the activation plot intercept point. In one embodiment, the method further comprises receiving configuration information indicative of the target recruitment level.

In one embodiment, each activation plot is indicative of a relationship between evoked responses of the neural tissue and a plurality of stimulus intensity levels, for one of a plurality of different postures of the patient. In one embodiment, the intercept stimulus intensity term is a positive non-zero value. In one embodiment, the method further comprises applying the neural stimulus to the neural tissue.

In accordance with another aspect of the present technology, there is provided an implantable device for controllably generating a neural stimulus. The neural stimulus being defined by at least one stimulus parameter. The device comprises a stimulator for generating the neural stimulus, for application to a neural tissue of a patient, via one or more stimulus electrodes in accordance with the at least one stimulus parameter. The device further comprises measurement circuitry for measuring an evoked response of the neural tissue, a communication port for receiving information from a data source, and a controller. The controller is configured to generate the at least one stimulus parameter, at a first stimulus intensity level, and measure a response of the neural tissue, evoked by the neural stimulus. The controller is further configured to determine a second stimulus intensity level, based on an activation plot intercept point, the first stimulus intensity level, the measured response of the neural tissue and a target recruitment level, and adjust the at least one stimulus parameter to the second stimulus intensity level.

In one embodiment, the activation plot intercept point indicates an intercept point for a plurality of activation plots associated with the neural tissue. In one embodiment, the device further comprises firmware for configuring the controller.

In accordance with another aspect of the present technology, there is provided a system for controlling a neural stimulus for application to a neural tissue of a patient, the neural stimulus being defined by at least one stimulus parameter. The system comprises a configuration module and an implantable device in electrical communication with the neural tissue. The configuration module comprises a transmission port for transmitting information indicative of an activation plot intercept point to the implantable device. The implantable device comprises a stimulator for generating the neural stimulus via one or more stimulus electrodes in accordance with the at least one stimulus parameter, measurement circuitry for measuring an evoked response of the neural tissue, a reception port for receiving information from the configuration module, and a controller. The controller is configured to generate the stimulus parameter, at a first stimulus intensity level, and measure a response of the neural tissue, evoked by the neural stimulus. The controller is further configured to determine a second stimulus intensity level, based on the activation plot intercept point, the first stimulus intensity level, the measured response of the neural tissue and a target recruitment level, and adjust the stimulus parameter to the second stimulus intensity level.

In one embodiment, the activation plot intercept point indicates an intercept point for a plurality of activation plots associated with the neural tissue. In one embodiment, the system further comprises a fitting module for determining the activation plot intercept point. The fitting module comprises instructions which, when executed by one or more processors, causes performance of the following, determining a plurality of activation plots, each activation plot based on one of a plurality of activation data sets, adjusting at least one of the plurality of activation plots, such that all of the plurality of activation plots, when extrapolated, intercept at an activation plot intercept point, and communicating information indicative of the activation plot intercept point to the implantable device.

In accordance with another aspect of the present technology, there is provided a method of controlling a neural stimulus, the neural stimulus being defined by at least one stimulus parameter. The method comprises determining a plurality of activation plots of a neural tissue of a patient, each activation plot based on one of a plurality of activation data sets, adjusting at least one of the plurality of activation plots, such that all of the plurality of activation plots, when extrapolated, intersect at an activation plot intercept point, and communicating information indicative of the activation plot intercept point to an implantable device, the implantable device being electrically connected to the neural tissue.

In one embodiment, the method further comprises generating, by the implantable device, a stimulus parameter, at a first stimulus intensity level, to control a stimulator that generates the neural stimulus for application to the neural tissue, and measuring, by the implantable device, a response of the neural tissue, the response being evoked by the neural stimulus. In one embodiment, the method further comprises determining, by the implantable device, a second stimulus intensity level, based on the activation plot intercept point, the first stimulus intensity level, the measured response of the neural tissue and a target recruitment level, and adjusting, by the implantable device, the stimulus parameter to the second stimulus intensity level.

In one embodiment, the activation plot intercept point indicates an intercept point for a plurality of activation plots associated with the neural tissue. In one embodiment, the steps of determining a plurality of activation plots, each activation plot based on one of a plurality of activation data sets, and adjusting at least one of the plurality of activation plots, such that all of the plurality of activation plots, when extrapolated, intersect at an activation plot intercept point, are performed by a fitting module.

In one embodiment, the implantable device is configured to execute the fitting module. In one embodiment, adjusting at least one of the plurality of activation plots comprises determining the intercept point for at least two of the plurality of activation plots, and adjusting the at least one of the plurality of activation plots to produce an adjusted activation plot, wherein the adjusted activation plot crosses the intercept point.

In one embodiment, the method further comprises empirically deriving a plurality of activation data sets, each activation data set of the plurality of activation data sets comprising information indicative of a plurality of data couples, each data couple comprising a neural stimulus intensity level and a measured response of the neural tissue, evoked by a neural stimulus applied at the neural stimulus intensity level, and each activation data set of the plurality of activation data sets being associated with one of a plurality of postures of the patient.

In accordance with another aspect of the present technology, there is provided a system for controlling a neural stimulus for application to a neural tissue of a patient, the neural stimulus being defined by at least one stimulus parameter. The system comprises means for determining a plurality of activation plots of a neural tissue of a patient, each activation plot based on one of a plurality of activation data sets, means for adjusting at least one of the plurality of activation plots, such that all of the plurality of activation plots, when extrapolated, intersect at an activation plot intercept point, and means for communicating information indicative of the activation plot intercept point to an implantable device, the implantable device being electrically connected to the neural tissue.

BRIEF DESCRIPTION OF DRAWINGS

The invention will now be described with reference to the accompanying drawings, in which.

DESCRIPTION OF EMBODIMENTS

Figure 1:
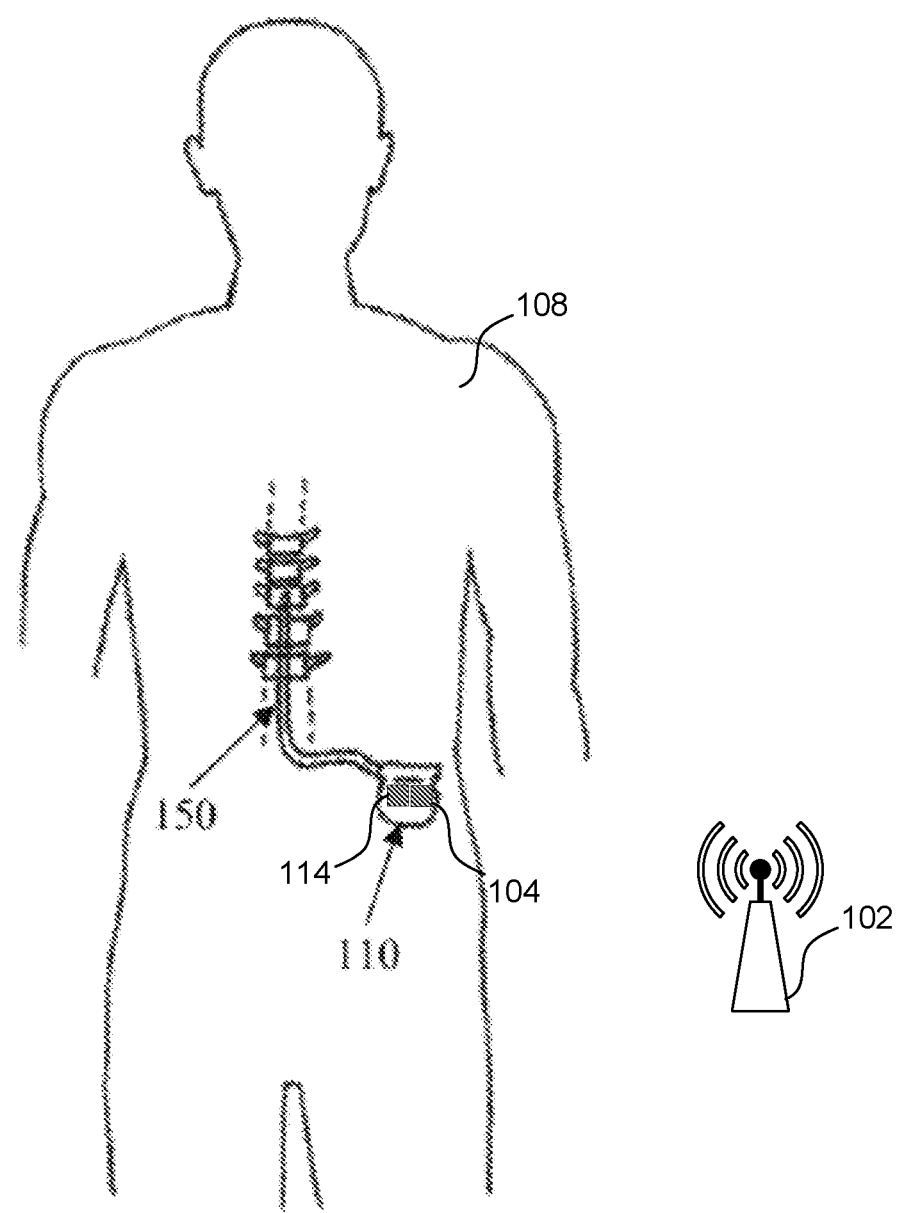
FIG. 1 schematically illustrates an implanted neural stimulator in a patient, according to an embodiment.

FIG. 1—Implanted Neural Stimulator Device

FIG. 1 schematically illustrates an implanted neural stimulator device in a patient 108, according to an embodiment. The stimulator comprises an electronics module 110 implanted at a suitable location. In one embodiment, the electronics module 110 is implanted in the patient's lower abdominal area or posterior superior gluteal region. In other embodiments, the electronics module 110 is implanted in other locations, such as a flank or sub-clavicular. The stimulator further comprises an electrode assembly 150 implanted within the epidural space and connected to the module 110 by a suitable lead. The stimulator further comprises an energy storage device 104 and a telemetry module 114. The energy storage device 104 may be any suitable energy storage device such as a battery or capacitor. The telemetry module 114 transfers power and/or data between an external device 102 and other modules of electronics module 110. For example, the energy storage device 104 may receive power from charger associated with the external device 102. The telemetry module 114 may utilise any suitable type of transcutaneous communication such as infrared (IR) and electromagnetic including capacitive and inductive transfer, to communicate with the external device 102.

In one embodiment, the external device 102 comprises a configuration module, which comprises a fitting module to configure or "program" the implanted neural stimulator. Components of the external device are described further, in relation to FIG. 14.

Figure 2:
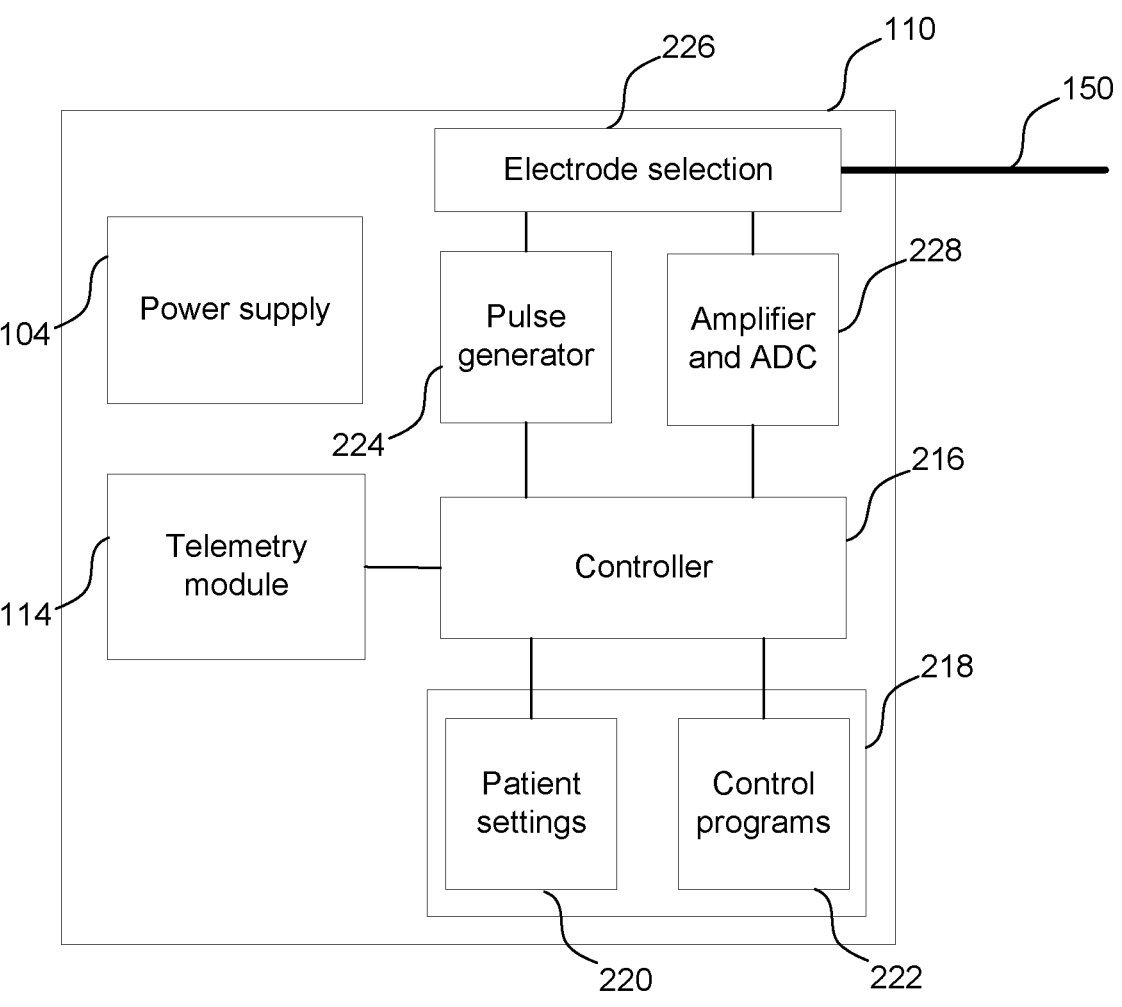
FIG. 2 is a block diagram of the implanted electronics module, according to an embodiment.

FIG. 2—Neural Stimulator Block Diagram

FIG. 2 is a block diagram of the implanted electronics module 110, according to an embodiment. Module controller 216 has an associated memory 218 storing patient settings 220, control programs 222 and the like. Controller 216 controls a pulse generator 224 to generate stimuli, such as current pulses, in accordance with the patient settings 220 and control programs 222. Electrode selection module 226 switches the generated pulses to stimulus electrode(s) of electrode array 150, for delivery of the current pulses to the tissue surrounding the stimulus electrode(s). Measurement circuitry 228 is configured to capture measurements of neural responses such as ECAPs sensed at sense electrode(s) of the electrode array as selected by electrode selection module 226.

Stimulating within a Therapeutic Range

For effective and comfortable operation of an implantable neural stimulation device, it is desirable to maintain stimulus intensity within a therapeutic range. A stimulus intensity within a therapeutic range may be above a recruitment threshold and below a comfort threshold for a patient.

A neural stimulation device can adjust the applied stimulus based on a feedback signal that is determined in light of the measured ECAP value, to keep the stimulus intensity within this therapeutic range, and approximate to a therapeutic stimulation level. A neural stimulation device that operates by adjusting the applied stimulus based on a measured ECAP value may be referred to as a closed loop neural stimulation (CLNS) device.

A CLNS device may configure a loop to calculate an error between a measured ECAP value and a target ECAP value. The neural stimulation device may adjust the applied stimulus intensity level to reduce the error as much as possible, such as by adding the weighted error to the present stimulus intensity level to increase or decrease the stimulus intensity level. However, as detailed below, adjusting the stimulation intensity level to maintain a constant (or near constant) measured ECAP value may not be sufficient to maintain a constant (or near constant) level of stimulation, as perceived by the patient, especially when the patient changes from one posture to another posture.

There is provided herein, an electronics module which includes a feedback loop controller configured to adjust the stimulation intensity level based on a neural recruitment calculation, rather than the calculation of an error between a target ECAP value and a measured ECAP value, to maintain a constant (or near constant) level of stimulation, as perceived by the patient.

Figure 3:
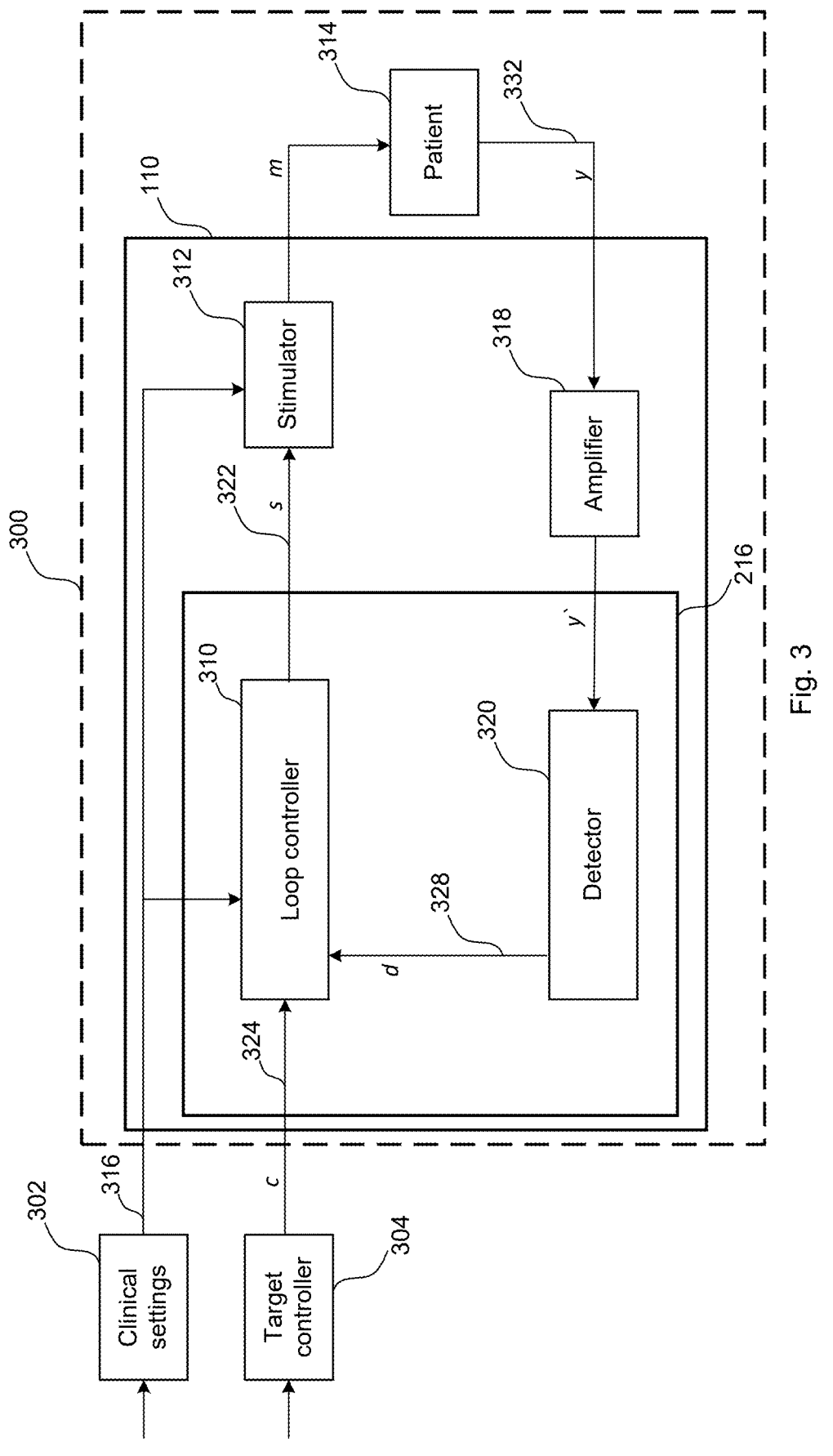
FIG. 3 is a system diagram illustrating a feedback loop of a stimulation device, according to an embodiment.

FIG. 3—Feedback Loop Pathway

FIG. 3 is a system diagram illustrating elements and inputs of a feedback loop 300 for adjusting a stimulus intensity level of a neural stimulus applied to the patient 314, according to an embodiment. The feedback loop 300 comprises an electronics module 110, a patient 314 and inputs, including a clinical settings controller 302 and a target controller 304. The electronics module comprises a stimulator 312 that takes a stimulus parameter s and converts it into a neural stimulus m. The stimulus parameter defines a stimulation pattern which produces an electrical pulse on stimulus electrodes. The stimulus parameter s may define an amplitude, or stimulus intensity level, of stimulus current. The stimulus parameter s may also define a pulse width, alternating phase on/off, number of phases, number of stimulus electrode poles (bipolar, tripolar etc.), stimulus position, stimulus to measurement distance and stimulus rate. The stimulus m output by the stimulator 312 has a summary value, usually the stimulus current, which is controlled by the loop controller 310 of the feedback loop 300.

The stimulus crosses from the electrodes to the spinal cord: however, the neural recruitment arising from this is affected by mechanical changes in the patient, including posture changes, walking, breathing, heartbeat and so on. Mechanical changes may cause impedance changes, or changes in the distance and orientation of the nerve fibres, affecting the neural recruitment and the measured evoked response generated by the neural recruitment.

Various sources of noise may add to the evoked response y before the response is measured, including: (a) artefacts, which, in some embodiments, are dependent on both stimulus current and posture: (b) electrical noise from external sources such as 50 Hz mains power: (c) electrical disturbances produced by the body such as neural responses evoked not by the device but by other causes such as peripheral sensory input, EGG, EMG; and (d) electrical noise from amplifier 318.

The ECAP value of the evoked response provides a measure d of the recruitment of the fibres being stimulated. The evoked response signal y 332 is amplified by the signal amplifier 318 and then measured by the detector 320. The detector 320 comprises measurement circuitry to measure the amplified response signal y' and to output a measured response, d 328, comprising an ECAP value. The measured response d 328 is input into the loop controller 310.

The loop controller 310 calculates an adjusted stimulus intensity level for stimulus parameter s 322, based on the measured response d 328, with the aim of providing neural stimulus at an intensity that allows the patient 314 to receive consistent comfortable and therapeutic stimulation.

Two clocks (not shown) are used in this embodiment, being a stimulus clock operating at ~60 Hz and a sample clock for measuring the evoked response operating at ~10 KHz. As the detector is linear, only the stimulus clock affects the dynamics of the feedback loop 300. On the next stimulus clock cycle, the stimulator 312 outputs stimulus in accordance with the adjusted stimulus parameter. Accordingly, there is a delay of one stimulus clock cycle before the stimulus is updated in light of the loop controller 310 adjusting the stimulus intensity level of the stimulus parameter 322.

Figure 4:
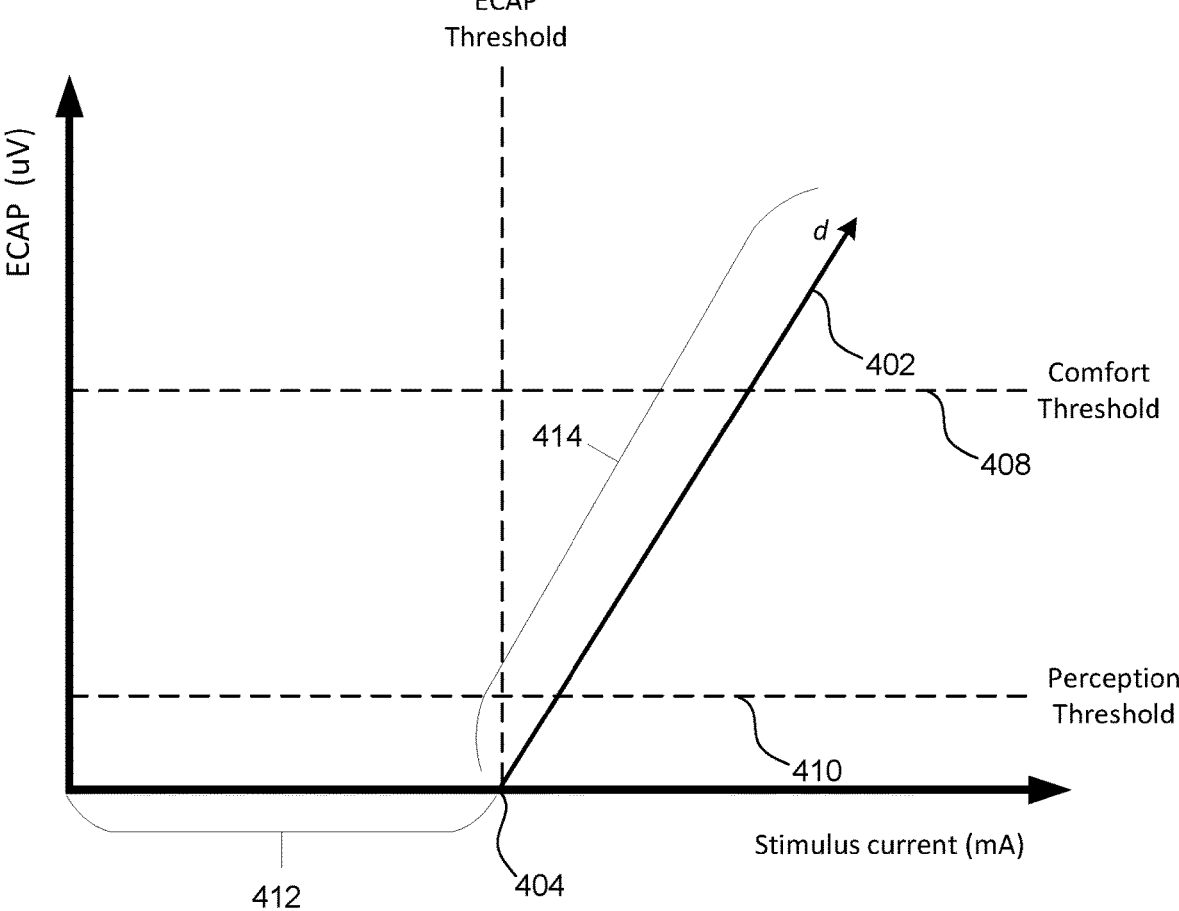
FIG. 4 illustrates an activation plot, according to an embodiment.

FIG. 4—Activation Plot

FIG. 4 illustrates an activation plot 402, according to an embodiment. An activation plot is a representation of the relationship between stimulus intensity level (i.e. stimulus current amplitude) and the stimulation response intensity (i.e. ECAP value) evoked by the stimulus. An activation plot is dependent upon the posture of the patient. Accordingly, a patient may be associated with a plurality of activation plots, one activation plot for each of a plurality of postures of the patient.

Activation plot 402 indicates the relationship between measured response signal, d, as output from the detector 320, and stimulus current for a posture of the patient.

For each posture of the patient, there is a stimulation intensity which generates a field at which recruitment of neural fibres begins. At stimulation intensities above this threshold stimulation intensity, there is a relationship between the stimulus current and the measured evoked response. The threshold stimulation intensity may be referred to as the ECAP threshold 404.

The ECAP threshold 404 may be an inflection point on the activation plot 402, and may be referenced in terms of the measured ECAP value at the ECAP threshold, or in terms of the stimulus current value at the ECAP threshold (which is referred to herein as the threshold stimulus current). Defining the ECAP threshold in terms of the stimulus current has the advantage that the current stimulus current is directly available to the controller, while the measured ECAP value may be subject to a noise component.

Activation plot 402 includes a section 412 which has a zero ECAP value from the point at which the stimulus current is zero, until the ECAP threshold 404. For stimulus currents below the ECAP threshold 404, the detector 320 outputs an ECAP value of zero via the measured response signal, d 328. From the ECAP threshold 404, the activation plot 402 has an approximately constant slope 414 indicating an approximately linear relationship between stimulus current and the ECAP value of the measured response signal, d.

In some embodiments, the measured response signal may comprise an artefact component. If an artefact is adding a positive component to the measured ECAP value, the ECAP value corresponding to the ECAP threshold may have a positive value. Similarly, if an artefact is adding a negative component to the measured ECAP value, the ECAP value corresponding to the ECAP threshold may have a negative value.

An artefact component is not present in the embodiment illustrated in FIG. 4. Accordingly, the pre-threshold section 412 of the activation plot 402 tracks along the x-axis with an ECAP value of zero. If an artefact component is present, the detector 320 adjusts the evoked response signal y to negate the artefact component. Accordingly, for stimulus currents below the ECAP threshold, the measured response signal d 328 is equal to zero.

The activation plot 402 and the ECAP threshold 404 may be empirically derived through a process of providing stimulus to a patient in a particular posture, at increasing stimulus intensity levels, and measuring ECAP values to determine the stimulus intensity level at which the activation plot inflects to show a monotonically increasing relationship between stimulus intensity level and measured ECAP, for that posture.

Perception Threshold

FIG. 4 also illustrates an example comfort threshold 408, which is an ECAP value above which the patient experiences uncomfortable or painful stimulation, and an example perception threshold 410. The perception threshold corresponds to an ECAP value that may be perceivable by the patient. There are a number of factors which can influence the position of the comfort threshold and the perception threshold, including the posture of the patient.

Perception threshold 410 may correspond to a stimulus current that is greater than the stimulus current corresponding to the ECAP threshold 404, as illustrated in FIG. 4, if patient does not perceive low levels of neural activation. Conversely, the perception threshold may correspond to a stimulus current that is less than the stimulus current corresponding to the ECAP threshold 404, if the patient has a high perception sensitivity to low levels of neural activation.

Furthermore, the stimulus current corresponding to the ECAP threshold 404 may be greater than the stimulus current corresponding to the perception threshold if the signal to noise ratio of the evoked response signal y, input into the detector 320, is low.

Figure 5:
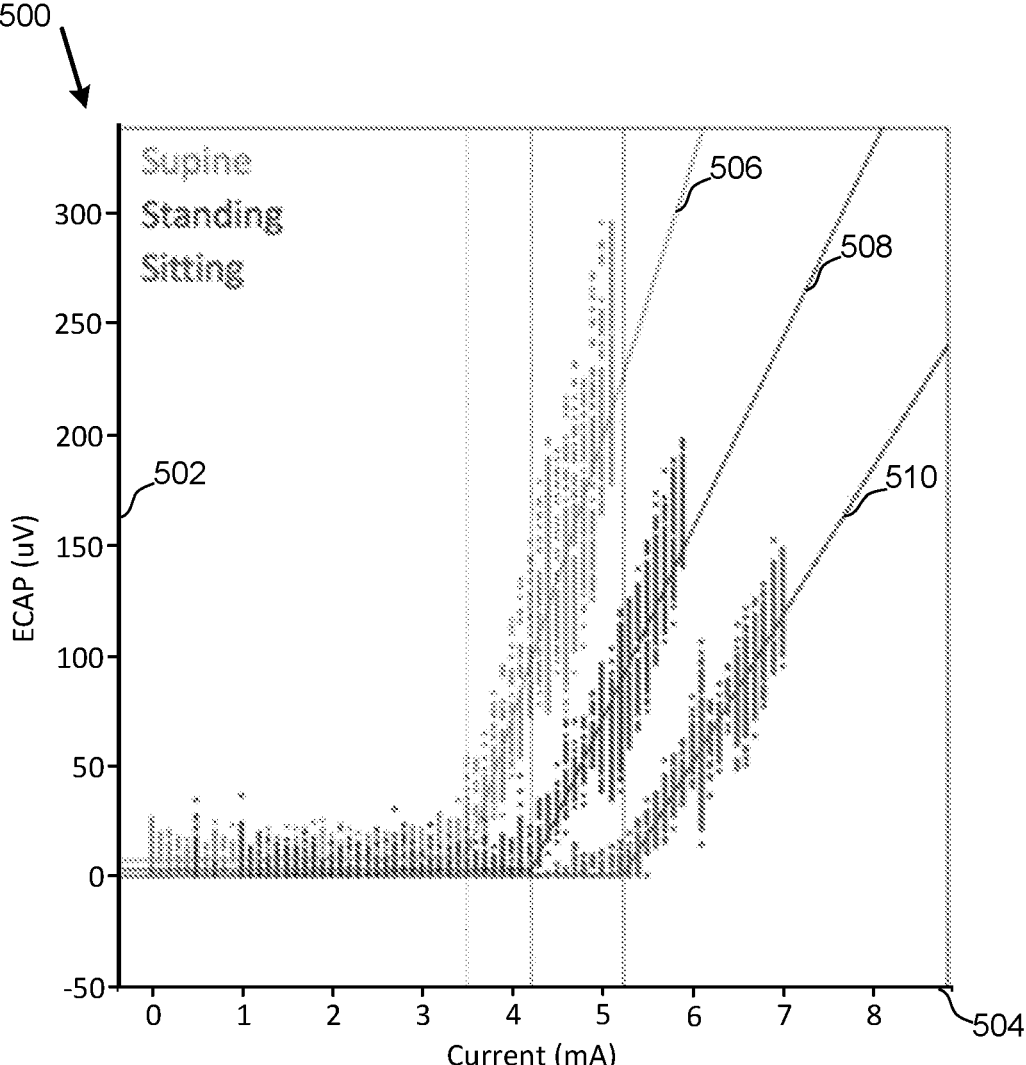
FIG. 5 illustrates activation plots derived from neural stimulation response data for a patient across multiple postures, according to an embodiment.

FIG. 5—An Activation Profile

FIG. 5 illustrates several activation plots derived from neural stimulation response data for a patient, according to an embodiment. FIG. 5 shows measured ECAP response d values, with reference to the y-axis 502, plotted against the intensity level of the stimulus (e.g. stimulus current in milliamps) that evoked the measured ECAP response d. The measured ECAP responses, plotted in graph 500 are plotted for activation data gathered while the patient was in different postures, when the patient's tissue is stimulated by a stimulation current s shown on the x-axis 504.

Line 506 is a linear approximation of the empirically derived data for the response of the patient's tissue, when the patient is in a supine posture. Accordingly, line 506 is an activation plot for the patient in the supine posture. In one embodiment, activation plot 506 is a line of best fit, or linear regression, with regard to the empirically derived data.

Activation plot 508 is a linear approximation of the empirically derived response data for the response of the patient's tissue, when the patient is in a standing posture. Activation plot 510 is a linear approximation of the empirically derived response data for the response of the patient's tissue, when the patient is in a sitting posture.

Activation plots 506, 508 and 510, in combination, form an activation profile associated with the patient.

Figure 6:
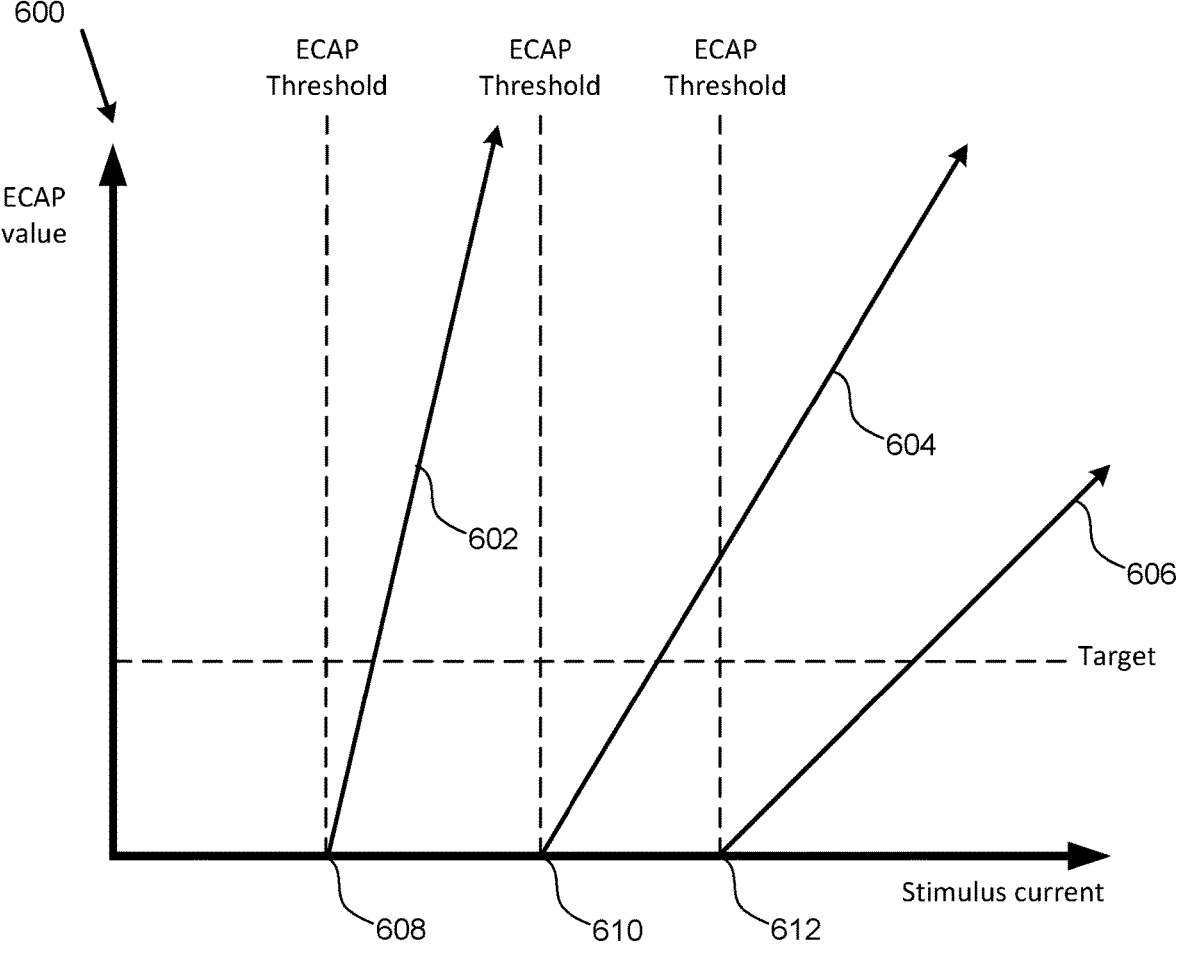
FIG. 6 illustrates the variation in the gradients and intercepts of activation plots with changing posture of the patient, according to an embodiment.

FIG. 6—Posture Changes

FIG. 6 illustrates the variation in the gradients of activation plots with changing posture of the patient, according to an embodiment. A change in posture may result from a macro level change in posture, i.e. a patient moving from a sitting posture to a standing posture. A change in posture may also result from a temporary physiological change of the patient, i.e. when sneezing, coughing or experiencing a change in heart rate. A change in posture of the patient may cause a change in impedance of the electrode-tissue interface or a change in the distance between electrodes and the neurons. While the activation plots for only three postures, 602, 604 and 606, are shown in FIG. 6, the activation plot for any given posture can lie between or outside the activation plots shown, on a continuously varying basis depending on posture. In one embodiment, as the patient's posture changes, the stimulus current at ECAP threshold changes, as indicated by the ECAP thresholds 608, 610 and 612. Additionally, as the patient's posture changes, the gradient of the response activation plot also changes, as indicated by the gradients of activation plots 602, 604 and 606. The stimulus current at the ECAP threshold, and the slope of the monotonically increasing section of the activation plot, both depend on the electrode-to-nerve distance and thus both vary with posture.

Neural Recruitment

Neural recruitment refers to the number of fibres recruited by a stimulus current provided by an implanted neural stimulator. The stimulus current, flowing through the one or more stimulus electrodes, generates a field at the patient neural tissue (e.g. the spinal cord). It will be appreciated that as the electrode changes distance with respect to the cord, the field changes. However, the stimulus current at which the field generated by the stimulus current begins to recruit fibres, for a specific posture of a patient, is the threshold stimulus current for that posture of the patient. At stimulus currents above the threshold stimulus current, the recruitment of the field generated by the stimulus current will be proportional to the ratio by which the stimulus current exceeds the threshold stimulus current.

Maintaining Constant Level of Recruitment

The recruitment of fibres begins at the same field intensity at the spinal cord regardless of the patient's posture. Therefore, the threshold stimulus current for a patient's posture provides a calibration point for estimating the level of recruitment of fibres resulting from stimulus current at a stimulus intensity level. Stimulus currents at levels above the threshold stimulus current, for a posture, create recruitment of fibres R, which may be estimated as:

$$R = \frac{I}{I_T} - 1 \qquad \text{(Equation 1)}$$

where I is a stimulus intensity level, and $I_T$ is the threshold stimulus intensity level, for the patient's posture.

Maintaining constant levels of neural recruitment, i.e. at a target recruitment level, may lead to a constant level of neural stimulation, as perceived by the patient.

Figure 7:
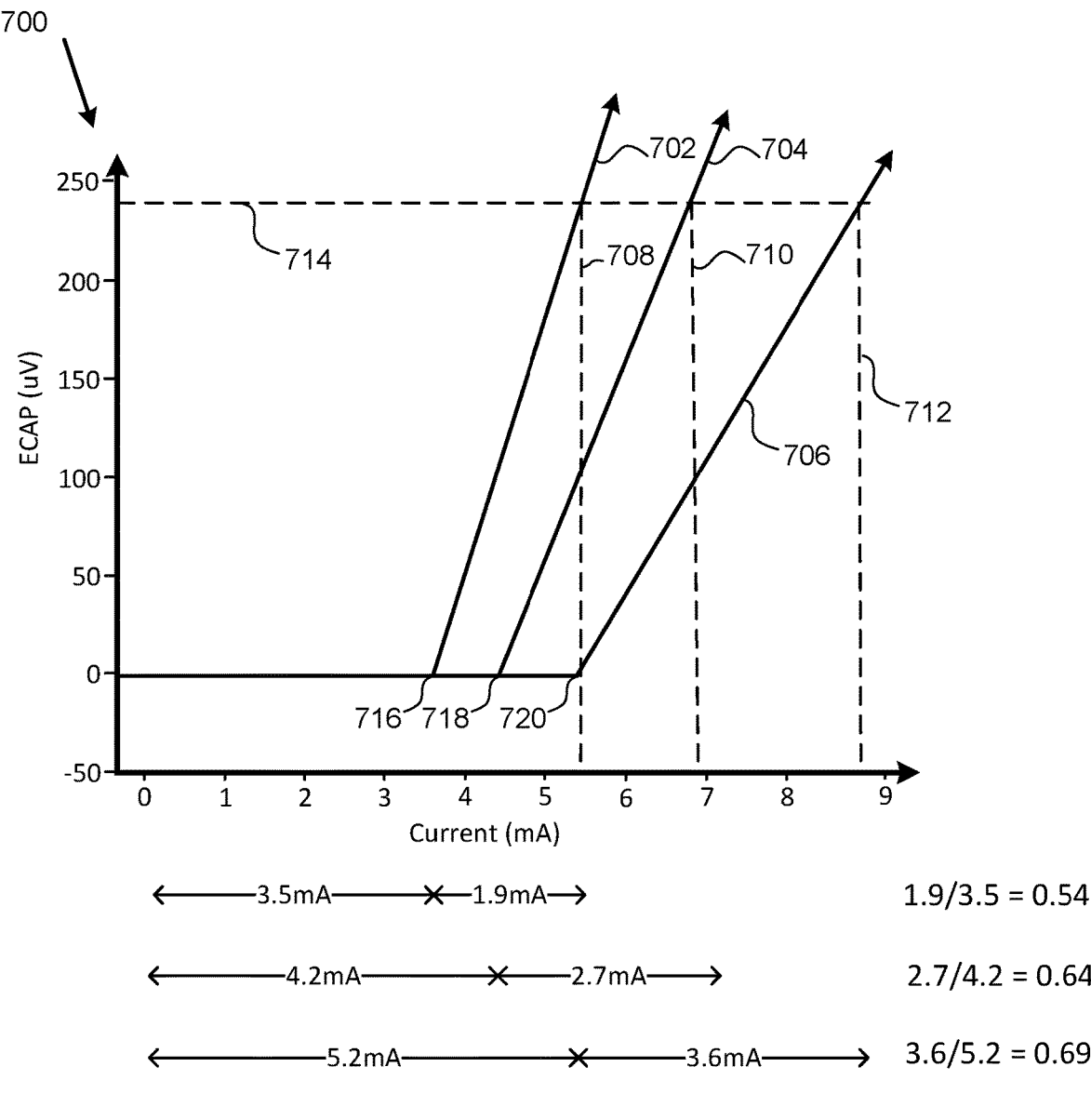
FIG. 7 shows activation plots for a patient in a supine, standing and sitting posture, according to an embodiment.

FIG. 7—Recruitment Level Falls with Posture Changes

If the patient moves into a less sensitive posture at a fixed level of stimulus, the neural recruitment decreases, and the measured ECAP value decreases. If the patient moves into a more sensitive posture, the neural recruitment increases, and the measured ECAP value increases. Although there may be alignment between the variation in ECAP value and the variation in neural recruitment due to posture changes, the relationship between these two measures is not proportional in all situations.

FIG. 7 shows activation plots, 702, 704 and 706, for a patient in a supine posture, a standing posture and a sitting posture, respectively, according to an embodiment. Dashed line 714 indicates a measured ECAP value of 240 µV.

The activation plot 702 for the supine (most sensitive) posture has an ECAP threshold 716 at 3.5 mA, and has a measured ECAP value of 240 µV when the stimulus current is 5.4 mA, as indicated by dashed line 708. Applying Equation 1, recruitment at a measured ECAP value of 240 µV, when the patient is in the supine posture, is equal to 0.54.

The activation plot 704 for the standing posture has an ECAP threshold 718 at 4.2 mA, and has a measured ECAP value of 240 µV when the stimulus current is 6.9 mA, as indicated by dashed line 710. Applying Equation 1, recruitment at a measured ECAP value of 240 µV when the patient is in the standing posture, is equal to 0.64.

The activation plot 706 for the sitting (least sensitive) posture has an ECAP threshold 720 at 5.2 mA, and has a measured ECAP value of 240 µV when the stimulus current is 8.8 mA, as indicated by dashed line 712. Applying Equation 1, recruitment at a measured ECAP value of 240 µV, when the patient is in the sitting posture, is equal to 0.69.

Accordingly, for the same ECAP value (e.g. 240 µV in the example of FIG. 7) the recruitment level of the fibres varies from 0.54 to 0.64 to 0.69 as the patient moves from one, most sensitive, posture to a second and a third, least sensitive, posture. In the example of FIG. 7, the recruitment level of the fibres increases as the patient moves from the supine (most sensitive) posture, to the standing posture, and then to the sitting (least sensitive) posture.

Accordingly, a loop controller 310 that is configured to maintain a target ECAP level may result in the patient experiencing higher stimulation, in the form of a higher level of recruitment, for the same ECAP value, as the patient moves from a more sensitive posture to a less sensitive posture. A higher level of stimulation may be undesirable as it may exceed the patient's comfort threshold.

Recruitment Focused Feedback Loop

It may be advantageous for the stimulation device to provide neural stimulation that evokes a constant recruitment level, or at least a recruitment level within a small range, even as the patient changes posture. A constant recruitment level will allow the patient to experience a consistent level of therapeutic stimulation.

Furthermore, as described in U.S. Pat. No. 9,381,356, by the present applicant, the contents of which are incorporated herein by reference, in some situations it is desirable for the neural stimulation to follow a desired curve of therapeutic benefit, in which the value of the measured ECAP curves downward, from the left hand side to the right hand side of a graph of an activation plot, whilst the recruitment level remains stable, as the patient moves from a more sensitive posture to a less sensitive posture, thereby causing the distance between the electrode and the patient's spinal cord to increase.

Accordingly, there is provided herein, a neural stimulation electronics module that is configured to provide stimulation at stimulation intensity levels that evoke neural recruitment at a target recruitment level in the patient, even as the patient changes posture. Accordingly, the neural stimulation electronics module provided herein seeks to ameliorate the abovementioned issues associated with a CLNS feedback loop that is configured to maintain a target ECAP level.

Providing the Target Recruitment Level

Referring again to FIG. 3, the loop controller 310 receives input, via telemetry module 114, from a target controller 304 and a clinical settings controller 302.

The target controller 304 inputs a target recruitment level c 324 to the loop controller 310. In one embodiment, the target controller 304 provides an indication of a specific target recruitment level. In another embodiment, the target controller 304 provides an indication to increase or to decrease the present target recruitment level. The target controller 304 may comprise an input into the neural stimulation device, via which the patient or clinician can input a target recruitment level, or indication thereof. The target controller 304 may comprise memory in which the target recruitment level is stored, and provided to the loop controller 310.

A clinical settings controller 302 provides clinical settings to the system, including the gain value for the loop controller 310 and the stimulus parameters for the stimulator 312. The clinical settings controller 302 can be configured to adjust the gain value, K, of the loop controller 310 to compensate for patient sensitivity. The clinical settings controller 302 may comprise an input into the neural stimulation device, via which the patient or clinician can adjust the clinical settings. The clinical settings controller 302 may comprise memory, in which the clinical settings are stored, and are provided to components of the electronics module 110.

Complex Calculations for Posture Movements, and In-Between Postures

If the loop controller 310 knows the threshold stimulus current $I_T$ for the current posture of the patient, the loop controller 310 can determine a suitable stimulus intensity level to evoke a target neural recruitment level by applying Equation 1.

As noted above, threshold stimulus currents $I_T$ can be determined by empirically deriving neural stimulus response data, and deriving an activation profile for the patient, the activation profile comprising an activation plot for each of a plurality of postures of the patient.

However, it is often desirable that a patient receive therapeutic stimulation even when the patient moves to a posture for which an activation plot has not been empirically derived (for example, a half-standing, half-sitting posture), or as the patient transitions between one posture to another posture.

The calculation to determine the threshold stimulus current $I_T$ for 'additional' or 'in-between' postures can be complex due to a lack of simple mathematical relationship between the activation plots. Accordingly, it may be difficult to configure the loop controller 310 to determine adjustments to the stimulus intensity level to maintain the target neural recruitment, as the patient changes posture.

Complex calculations require complex programming, more processor cycles to calculate and an associated increased requirement for power and memory. Accordingly, it is desirable to simplify the calculations performed by the loop controller for determining adjustments to the stimulation intensity level.

Provided herein is a method for simplifying the calculations performed by the loop controller 310, by ensuring a mathematical relationship between the activation plots within a single activation profile for a patient. The adjustment of the activation plots of the activation profile to ensure the linear activation plots intersect at a common point simplifies the calculations performed by the stimulation device.

Figure 8:
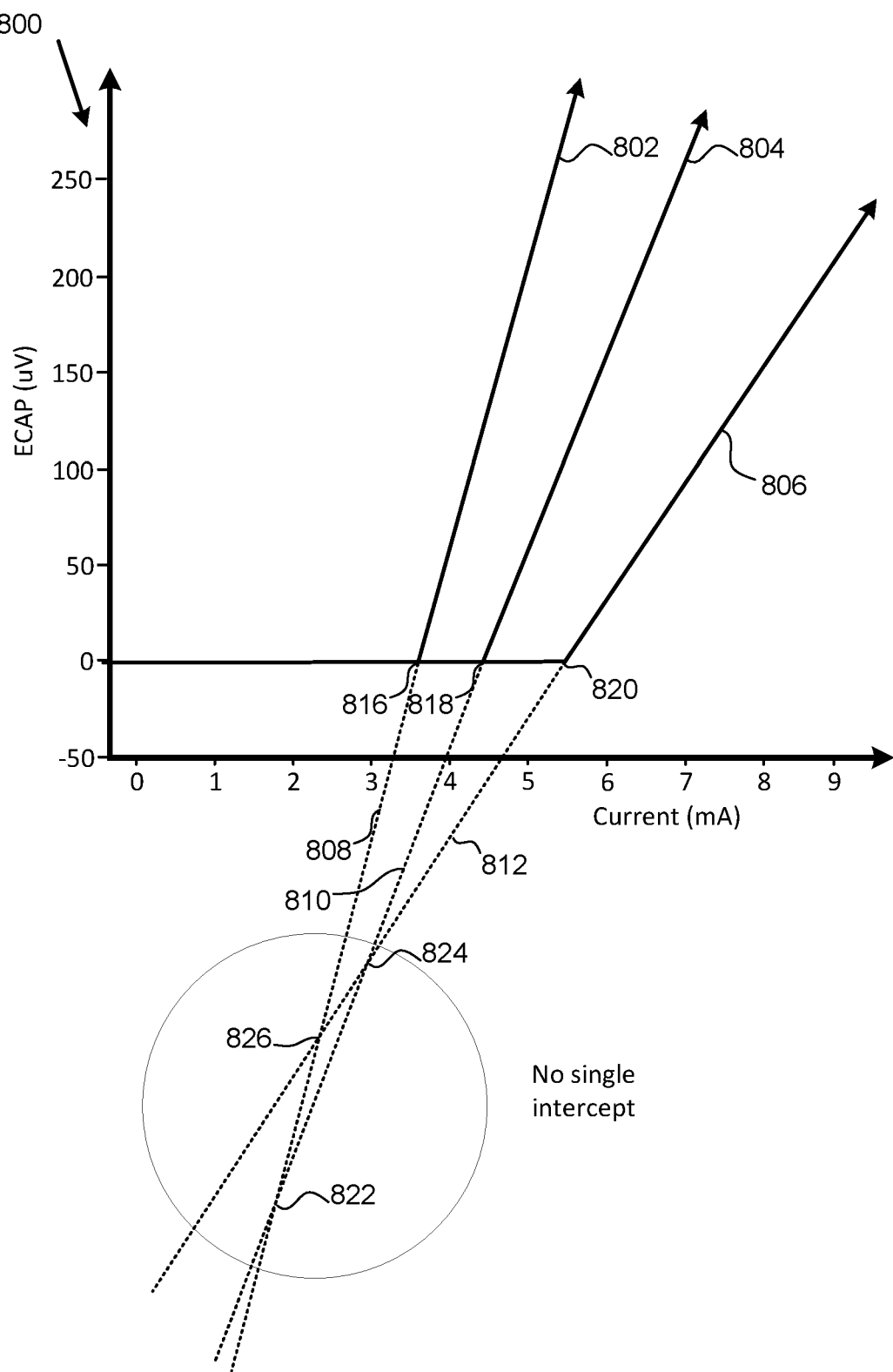
FIG. 8 shows extrapolated activation plots, for a patient in a supine, standing and sitting posture, according to an embodiment.
Figure 9:
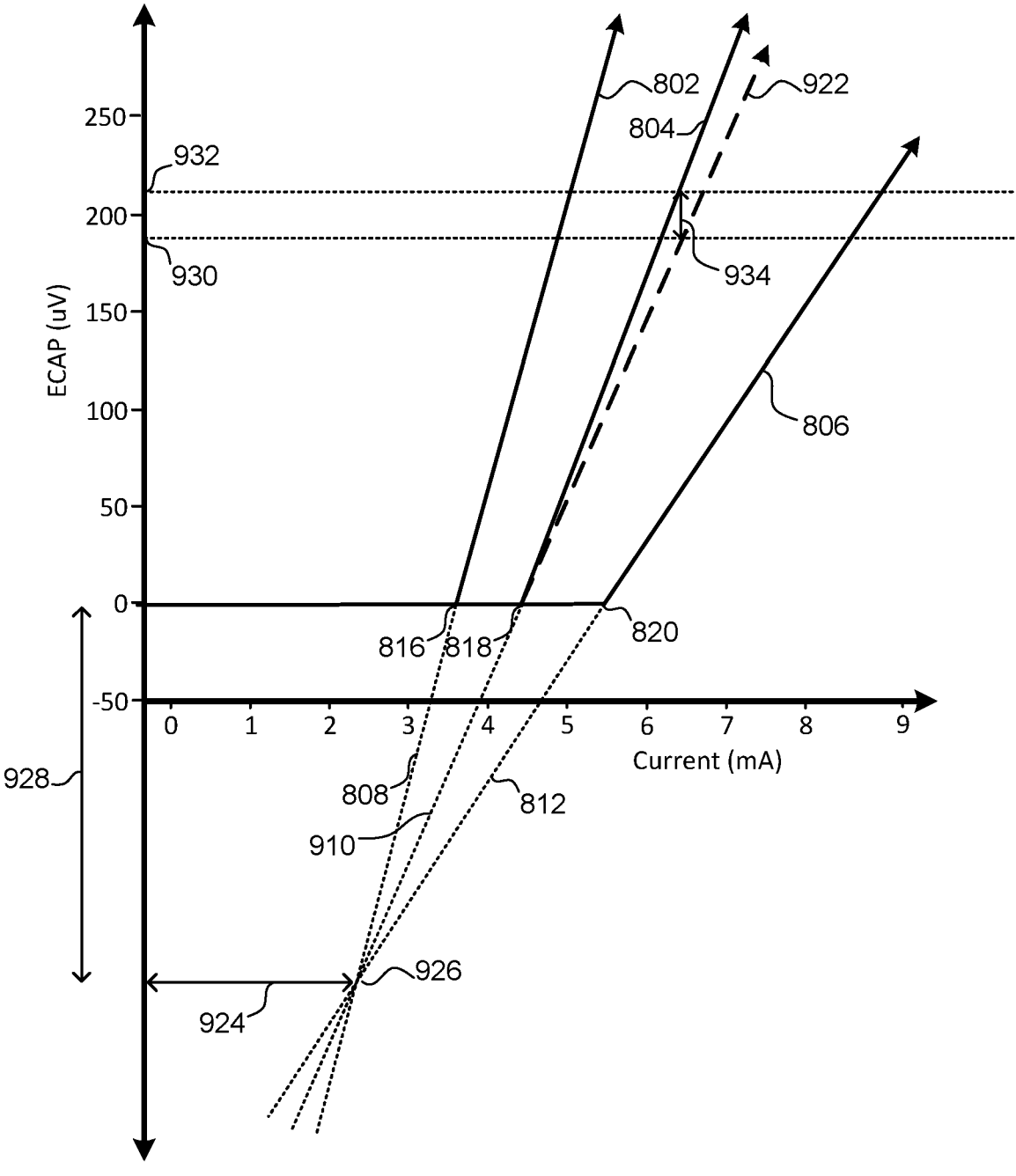
FIG. 9 shows the adjustment of the activation plot of FIG. 8 to produce an adjusted activation plot, according to an embodiment.

The activation profile adjustment will be described with regard to an embodiment as illustrated in FIGS. 8 and 9.
FIG. 8—Extrapolation of Activation Plot Lines FIG. 8 shows activation plots, 802, 804 and 806, which correspond to the patient being in a supine, standing and sitting posture, respectively, according to an embodiment. Each of the activation plots, 802, 804 and 806, comprise a horizontal linear section at an ECAP value of 0 μV. Each of the activation plots, 802, 804 and 806, further comprise a monotonically increasing section, which starts at the ECAP threshold for each of the activation plots.

FIG. 8 further shows an extrapolated section of the monotonically increasing section of each activation plot. For example, activation plot 802 has been extrapolated from ECAP threshold 816, along line 808. Similarly, activation plot 804 has been extrapolated from ECAP threshold 818, along line 810, and activation plot 806 has been extrapolated from ECAP threshold 820, along line 812.

The extrapolated sections do not intersect at a single common intercept point. The extrapolated sections of activation plots 802 and 804, namely 808 and 810, intersect at point 822. The extrapolated sections of activation plots 804 and 806, namely 810 and 812, intersect at point 824. The extrapolated sections of activation plots 802 and 806, namely 808 and 812, intersect at point 826.

Each of the activation plots shown in FIG. 8 has been individually derived as a linear approximation of empirically derived data for a patient in a particular posture. Accordingly, there is no simple mathematical relationship between the activation plots 802, 804 and 806.

As described in International Patent Publication no. WO2022/040757, to calculate adjustments to the stimulus intensity level to achieve a target recruitment level, based on the activation plots similar to 802, 804 and 806, exponential powers can be applied to compute feedback terms: however, this computation of feedback terms requires the use of exponential and logarithmic functions. Exponential or logarithmic functions may, for some implementations, be too computationally complex to perform efficiently on a small, low-power microcontroller configured to control the feedback loop. Accordingly, the methods of control of the feedback loop 300, provided herein, may provide a useful alternative to the methods utilising exponential or logarithmic functions.
Forming an Activation Plot Intercept Point An activation plot comprises a post-threshold section of the plot, extending from the ECAP threshold point of the activation plot. To simplify the calculations to adjust the stimulus intensity level, it may be desirable for the activation plots, associated with the various postures of a patient, to be configured such that, when the post-threshold section of the plot is extrapolated downwards, with respect to the y-axis, the extrapolated post-threshold sections of each of the activation plots intersect at a common intercept point.

This common intercept point provides a mathematical relationship between the activation plots. The common intercept point also provides a relationship between the threshold stimulus current for the current posture and a measurement of a neural response and the stimulus intensity level that evoked it, and this relationship can be exploited to simplify the calculations performed by the stimulation device to adjust the stimulation intensity level to maintain a target recruitment level evoked by the neural stimulus.
FIG. 9—Example Adjustment of Activation Profile To provide a relationship between the activation plots, one or more of the activation plots of FIG. 8 may be adjusted, or re-calculated, such that all three activation plots intersect at a single common intercept point.

FIG. 9 shows the adjustment of activation plot 804 to produce adjusted activation plot 922, such that the extrapolated linear sections, 808 and 812, of activation plots 802 and 806, and the extrapolated linear section 910 of adjusted activation plot 922 all intersect at a common intercept point, being intercept point 926 in this example.

Intercept point 926 can be represented by Cartesian coordinates which define the distance 924 along the x-axis from a stimulus current of 0 mA, and the distance 928 along the y-axis from an ECAP value of 0 μV. With regard to the example shown in FIG. 9, the Cartesian coordinates for the intercept point 926 are $(I_0, -E_0) = (2.3, -190)$.

Adjusted activation plot 922 deviates marginally from activation plot 804, as is demonstrated by deviation 934. A loop controller providing a stimulus current of approximately 6.5 mA, for the posture associated with adjusted activation plot 922, would expected to measure an ECAP response of 190 μV, as indicated by 930. However, if activation plot 804 is more accurately representative of the neural response of the patient's tissue, at this stimulation intensity, in this posture, then the measured response may be closer to 210 μV, as indicated by 932. As the activation plots are linear representations of non-linear empirically derived data, a margin of error between the expected measured ECAP response and the actual ECAP response is to be expected, and accommodated by the adjustments made to the stimulus intensity level by the loop controller 310.
Deriving Adjusted Activation Profile Through a Fitting Process In one embodiment, baseline activation plots for a patient are derived by a fitting module, based on activation data sets obtained during a fitting process in which ECAP values corresponding to a range of stimulus intensity levels are measured for a plurality of different postures of the patient. The baseline activation plots may each be derived as a linear approximation of the empirically derived activation data sets.

In one embodiment, the fitting module comprises an activation plot adjustment module (APAM), configured to adjust one or more of the baseline activation plots to ensure that the adjusted activation profile comprises activation plots that have a common intercept point.

In one embodiment, the fitting module communicates adjusted activation profile information (AAPI) to the loop controller 310. The AAPI comprises an indication of the adjusted activation profile, including information indicative of the intercept point. In one embodiment, the information indicative of the intercept point comprises an intercept stimulus intensity level term $I_0$, and an intercept evoked response term $E_0$.

The loop controller 310 uses the AAPI to adjust the stimulation intensity level, based on the measured ECAP response. The fitting module, fitting process and AAPI are described further, in relation to FIGS. 13 and 14.

Adjusting the Stimulus Intensity Level to Maintain the Target Recruitment Level

During neural stimulation, the loop controller 310 aims to maintain stimulation at an intensity level that recruits fibres at (or approximate to) a target recruitment level, that provides therapeutic stimulation to the patient. To maintain a target recruitment level as the patient adjusts posture from a first posture to a second posture, the loop controller 310 adjusts the stimulation intensity to evoke an ECAP value that is associated with the target recruitment level for the second posture.

The loop controller 310 uses the AAPI and the principles of similar triangles, to calculate the threshold stimulus current $I_{T_2}$ for an activation plot associated with the patient's second posture.

$$\frac{E_{12}}{(I_1 - I_{T_2})} = \frac{E_0}{(I_{T_2} - I_0)} \qquad \text{(Equation 2)}$$

Where $I_0$ is the intercept stimulus intensity level term, $E_0$ is the intercept evoked response term, $I_1$ is a first stimulus intensity level, $I_{T_2}$ is the threshold stimulus current for an activation plot associated with the patient's second posture, and $E_{12}$ is a measured ECAP value evoked by a stimulus parameter generated at stimulus intensity level $I_1$ while the patient is in the second posture.

Rearranging Equation 2 provides Equation 3, which determines the threshold stimulus current $I_{T_2}$ for an activation plot associated with the second posture of the patient.

$$I_{T_2} = \frac{E_0 I_1 + I_0 E_{12}}{E_{12} + E_0} \qquad \text{(Equation 3)}$$

The recruitment level $R_{12}$ resulting from the present stimulation intensity level $I_1$, while the patient is in the second posture, can be determined from Equation 4.

$$R_{12} = \frac{I_1}{I_{T_2}} - 1 \qquad \text{(Equation 4)}$$

The loop controller 310 applies Equation 5 to determine the second stimulus intensity level $I_2$, which is expected to provide the target recruitment level $R_D$, while the patient is in the second posture.

$$I_2 = I_{T_2}(R_D + 1) \qquad \text{(Equation 5)}$$

To determine the expected ECAP value $E_2$ for a stimulus intensity level I, the loop controller may apply Equations 6 and 7, $$S = \frac{E_{12}}{I_1 - I_{T_2}} \qquad \text{(Equation 6)}$$

$$E_2 = S(I - I_{T_2}) \qquad \text{(Equation 7)}$$

where S is the gradient of the approximately constant slope (e.g. slope 414) of an activation plot, indicating an approximately linear relationship between stimulus current I and the measured ECAP value E.

Advantages of a Recruitment Focused Feedback Loop

As recruitment is the parameter controlled by the loop controller 310, then the recruitment is the same for both postures and there is no increase in perceived stimulation intensity with higher distance from the electrode to the cord, as would be the case for a feedback loop controlled by ECAP value.

Also, as the recruitment is the parameter controlled by the loop controller 310, and this is defined as the proportional extent to which the current exceeds the threshold, and the loop can calculate the threshold at each point, the loop gain will only vary due to the error between the approximation of the activation plot and the actual one.

FIG. 11—Example

Figure 11:
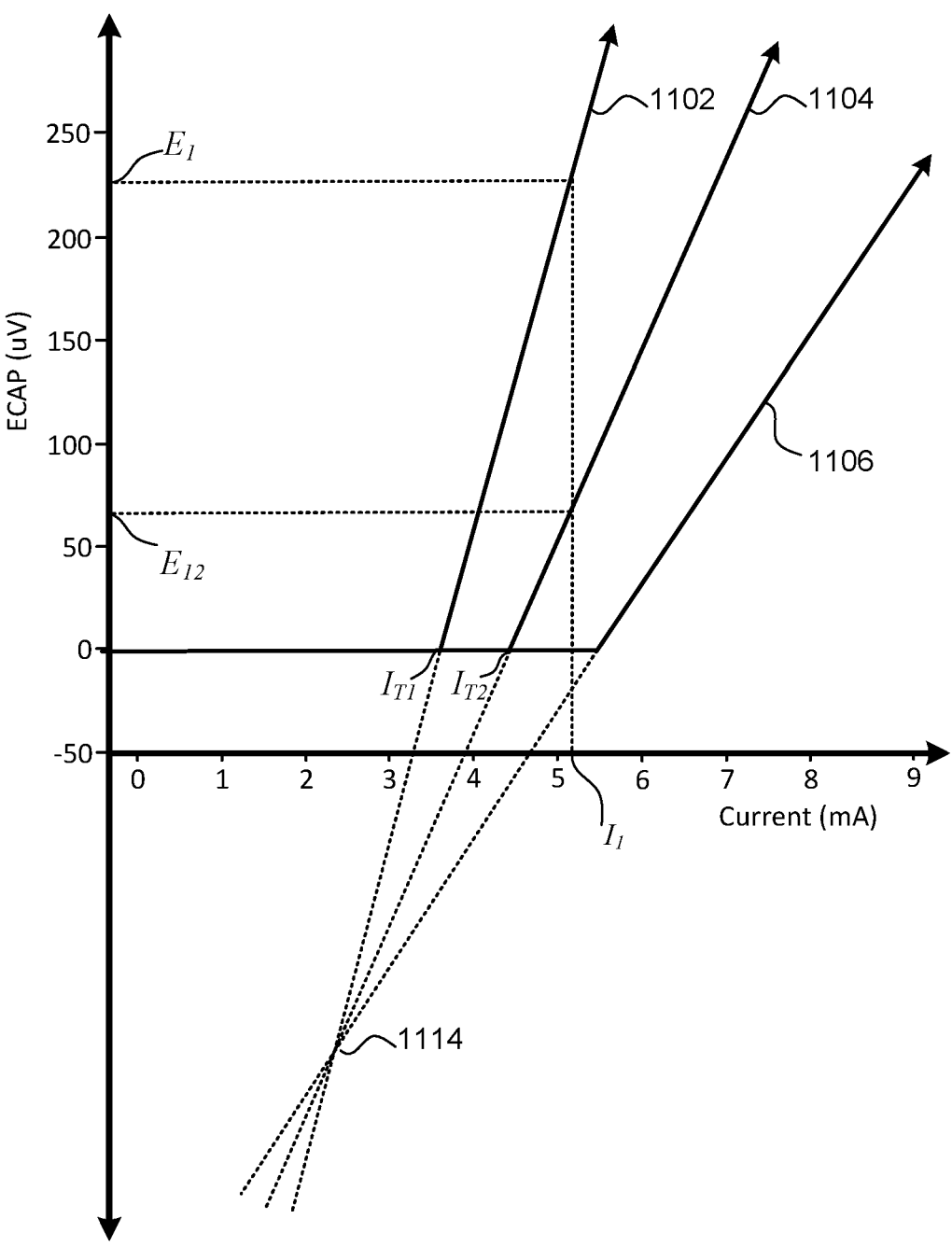
FIG. 11 shows the change in stimulation intensity level, to maintain a target recruitment level, as the patient transitions from a first posture to a second posture, according to an embodiment.

FIG. 11 is a graph showing the change in stimulation intensity level, to maintain a target recruitment level, as the patient transitions from a first posture to a second posture, according to an embodiment. FIG. 11 shows activation plots 1102, 1104, and 1106 associated with three postures of a patient. The activation plots, when extrapolated, all intersect at a common intercept point 1114, which is denoted by $(I_0, -E_0)$.

Initially, the patient is in a first posture, which is associated with an activation plot 1102 having a threshold stimulus current of $I_{T1} = 3.6$ mA. The stimulator is providing a stimulus current at $I_1 = 5.15$ mA and the measured ECAP value is $E_1 = 225$ µV. In this first posture, with the stimulus current at $I_1 = 5.15$ mA, the stimulation is producing the recruitment level of approximately 0.43. For the purposes of this example, this recruitment level is considered to be the patient's target (desired) recruitment level $R_D$.

The patient moves to a second posture, associated with activation plot 1104. The threshold $I_{T2}$ of the activation plot 1104, associated with the second posture, is greater than the threshold $I_{T1}$ of the activation plot 1102, associated with the patient's first posture.

In the second posture, the stimulus current at $I_1 = 5.15$ mA, produces a measured ECAP value $E_{12} = 70$ µV, which is lower than the measured ECAP value $E_1 = 225$ µV when the patient was in the first posture.

The feedback controller 310 may then use Equation 3 to compute the threshold $I_{T2}$ of the activation plot 1104 associated with the second posture. The feedback controller 310 may then use Equation 5 to compute 12, the stimulus current that will produce the target recruitment level $R_D$. Finally, the feedback controller 310 may use Equations 6 and 7 to compute the new ECAP target value $E_2$ that will produce the target recruitment level $R_D$ in the second posture.

Figure 10:
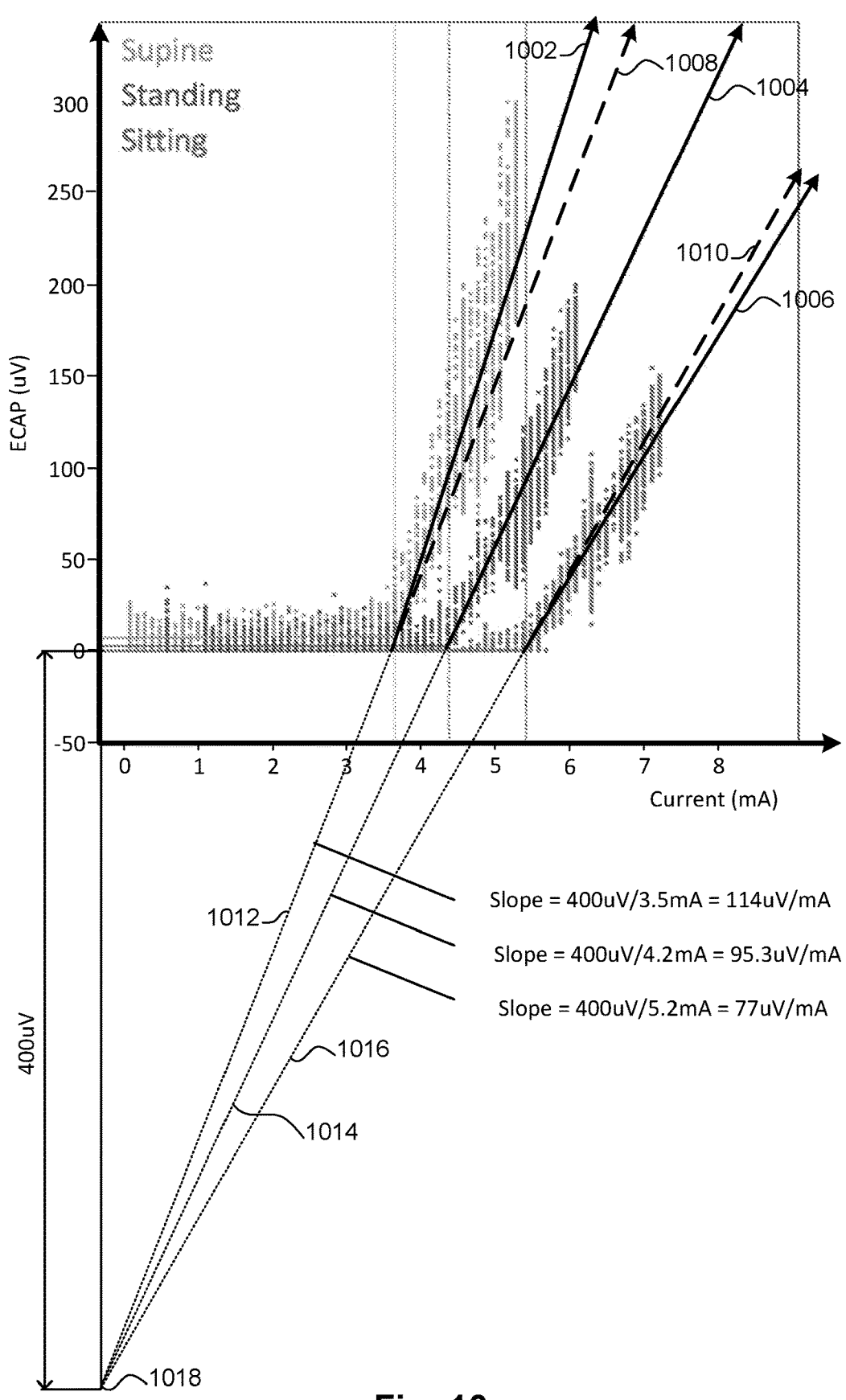
FIG. 10 shows extrapolated activation plots for a patient in a supine, standing and sitting posture, according to an embodiment.

FIG. 10—Intercept Point on y-Axis

FIG. 10 shows three activation plots, 1002, 1004 and 1006, which correspond to the patient being in a supine, standing and sitting posture, respectively, according to an embodiment. Each of the activation plots, 1002, 1004 and 1006, comprise a horizontal linear section at an ECAP value of 0 µV. Each of the activation plots, 1002, 1004 and 1006, further comprise a monotonically increasing linear section, which starts at the ECAP threshold for each of the activation plots.

FIG. 10 shows the adjustment of activation plot 1002 to produce adjusted activation plot 1008, and the adjustment of activation plot 1006 to produce adjusted activation plot 1010, such that the extrapolated linear sections, 1012, 1014 and 1016, of the activation plots 1008, 1004, and 1010 all intersect at a common intercept point, being intercept point 1018 in this example.

Intercept point 1018 is located on the y-axis and can be represented by Cartesian coordinates $(I_0, -E_0) = (0, -400)$.

As the intercept point 1018 is located on the y-axis, the intercept stimulus term $I_0$ is equal to zero. Reducing Equations 3 and 4, on the basis that $I_0 = 0$, indicates that when the intercept point is on the y-axis, the recruitment level is proportional to the ECAP for stimulus above the stimulus threshold for any posture.

Accordingly, when the intercept point is located on the y-axis, the measured ECAP value for a given recruitment does not exhibit the desired curve of therapeutic benefit, in which the measured ECAP for a given recruitment exhibits a downward curve, from the left hand side to the right hand side of a graph of an activation plot, as the patient moves from a more sensitive posture to a less sensitive posture.

Accordingly, in some embodiments, it may be preferable that the APAM sets the common intercept point at an offset from the y-axis. If the APAM sets the common intercept point on the y-axis, the loop controller 310 may implement a conventional feedback loop with a constant ECAP target value that is independent of posture.

Figure 12:
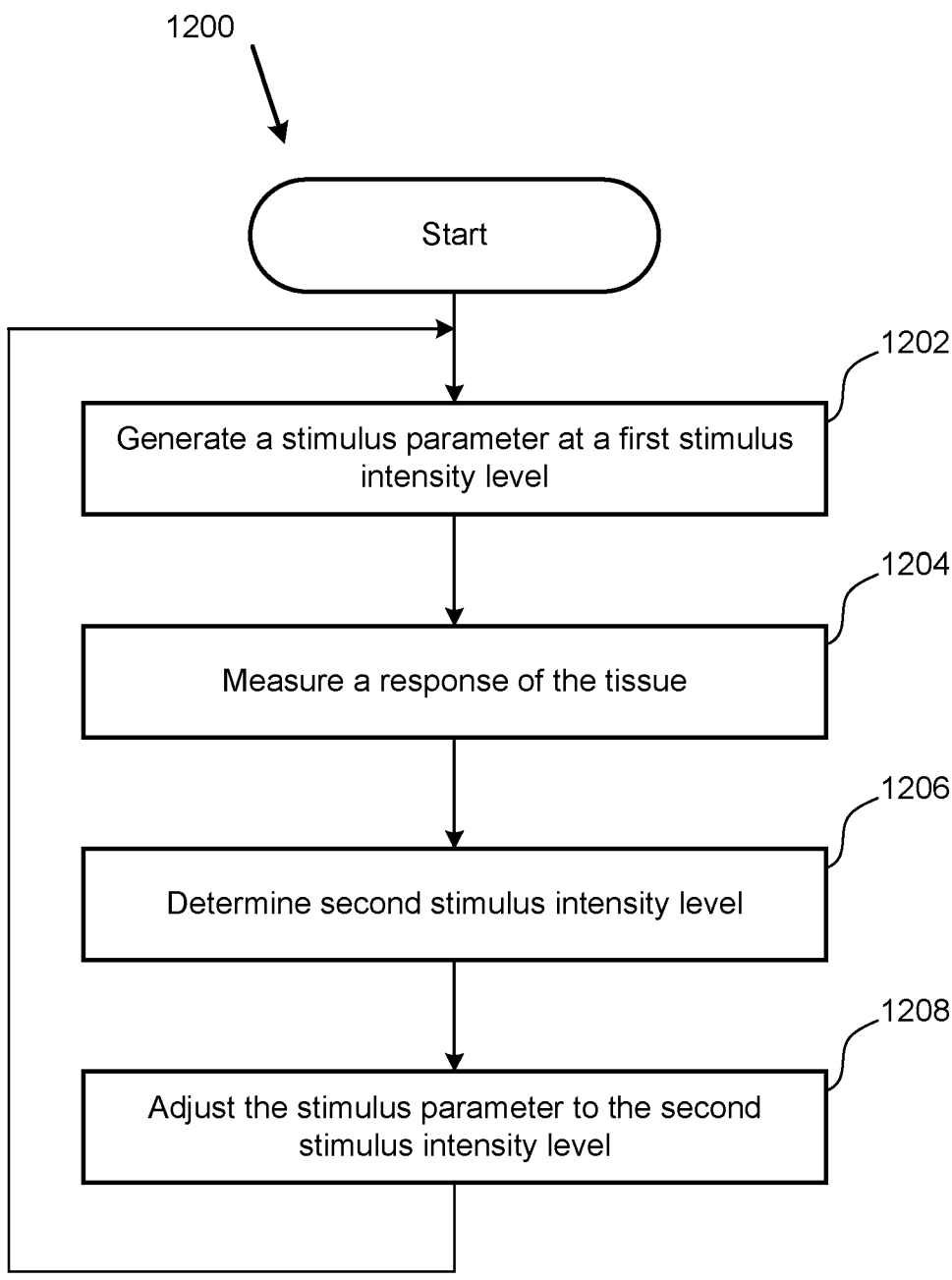
FIG. 12 illustrates a method of controlling a neural stimulus as described with reference to FIGS. 2 and 3, according to an embodiment.

FIG. 12—Method Performed by the Loop Controller

FIG. 12 illustrates a method 1200 of controlling a neural stimulus as described with reference to FIGS. 2 and 3, according to an embodiment. The neural stimulus is defined by at least one stimulus parameter. The method is performed by the controller 216 in that the controller 216 generates 1202 a stimulus parameter, at a first stimulus intensity level, to control a stimulator 312 that generates neural stimulus for application to a neural tissue of a patient 314. In step 1204, the controller 216 measures the response of the tissue, evoked by the neural stimulus. In step 1206, the controller 216 determines a second stimulus intensity level, based on an activation plot intercept point, the first stimulus intensity level, the measured response of the tissue, and a target recruitment level, and in step 1208, the controller 216 adjusts the at least one stimulus parameter to the second stimulus intensity level. The activation plot intercept point indicates a common intercept point for a plurality of activation plots associated with the tissue.

Figure 13:
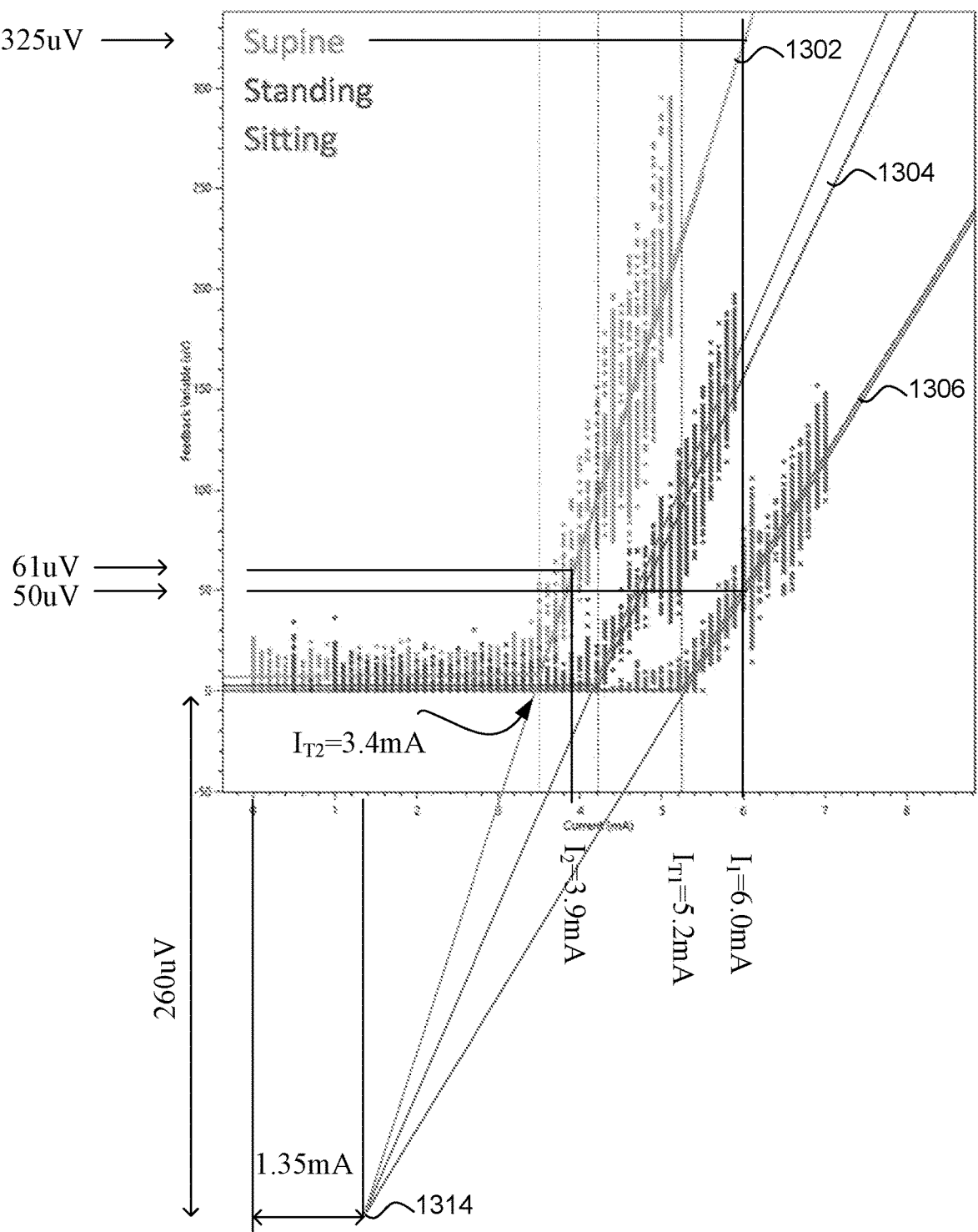
FIG. 13 shows the change in stimulation intensity level, to maintain a target recruitment level, as the patient transitions from a first posture to a second posture, according to an embodiment.

FIG. 13—Iterative Application of Method 1200

In one embodiment, the controller 216 performs method 1200 iteratively to provide therapeutic stimulation to a patient. An example of performing method 1200 iteratively is provided with reference to a situation shown in FIG. 13.

FIG. 13 shows three adjusted activation plots 1302, 1304, and 1306 associated with three postures of a patient (supine, sitting and standing respectively). The adjusted activation plots 1302, 1304, and 1306, when extrapolated, all intersect at a common intercept point 1314, which is denoted by $(I_0, -E_0)$ where $I_0 = 1.35$ mA and $E_0 = 260$ μV.

FIG. 13 illustrates where, in step 1202, the controller 216 generates a stimulus parameter at a first stimulus intensity level of 6 mA. In step 1204, the controller 216 uses the detector 320 to measure the response of the tissue to the stimulus. The response is measured as an ECAP value of 50 μV.

In step 1206, the controller 216 uses the loop controller 310 to determine a second stimulus intensity level. More specifically, the loop controller 310 determines the threshold stimulus current for the current posture of the patient by solving Equation 3, which indicates that the threshold stimulus current is 5.25 mA. This indicates that the patient is in the sitting posture. The loop controller 310 further determines the present recruitment level of the tissue by solving Equation 4, which indicates that the recruitment level is 0.14 units. In this example, the recruitment target is set to $R_D = 0.14$, as the patient finds this level of recruitment to be therapeutic.

In step 1206, the loop controller 310 determines a second stimulus intensity level to achieve the recruitment target. In one embodiment, the loop controller may do this by solving Equations 4, 3 and 5; however, as the first stimulus intensity level is producing recruitment at the target level, the loop controller 310 may set, in step 1208, the second stimulus intensity level to be the same as the first stimulus intensity level.

Assume the patient then changes posture to a supine posture and the method 1200 restarts by generating, at step 1202, a stimulus parameter at the first stimulus intensity level of 6 mA. In step 1204, the controller 216 uses the detector 320 to measure the response of the tissue to the stimulus. The response is measured as an ECAP value of 325 μV.

In step 1206, the controller 216 uses the loop controller 310 to determine a second stimulus intensity level. More specifically, the loop controller 310 determines the threshold stimulus current for the current posture of the patient by solving Equation 3, which indicates that the threshold stimulus current is 3.4 mA. The loop controller 310 may further determine the present recruitment level of the tissue by solving Equation 4, which indicates that the recruitment level is 0.756 units, indicating the perceived stimulation intensity is well above the recruitment target $R_D = 0.14$.

The loop controller 310 further determines the stimulus intensity level required to achieve the recruitment target of 0.14 units, by solving Equation 5, which indicates that the second stimulus intensity level is 3.9 mA. The second stimulus intensity level is lower than the first stimulus intensity level of 6 mA, being currently provided.

In step 1208, the controller 216 adjusts the stimulus parameter s to be the second stimulus intensity level, of 3.9 mA. In the supine posture, the ECAP evoked in response to stimulus at the second stimulus intensity level is 61 μV, as determined by Equation 6 and Equation 7.

Loop Response Time

To avoid sudden changes in stimulus current, the loop controller 310 may gradually adjust the stimulus current from $I_1$ to $I_2$ in increments, over a period of time. For example, the stimulus current may be adjusted according to a feedback term $k(I_1 - I_2)$, where the value k is chosen to set the response time of the feedback loop. Other PID type controls may be implemented, to improve response time, the smoothness of the response and other factors.

Figure 14:
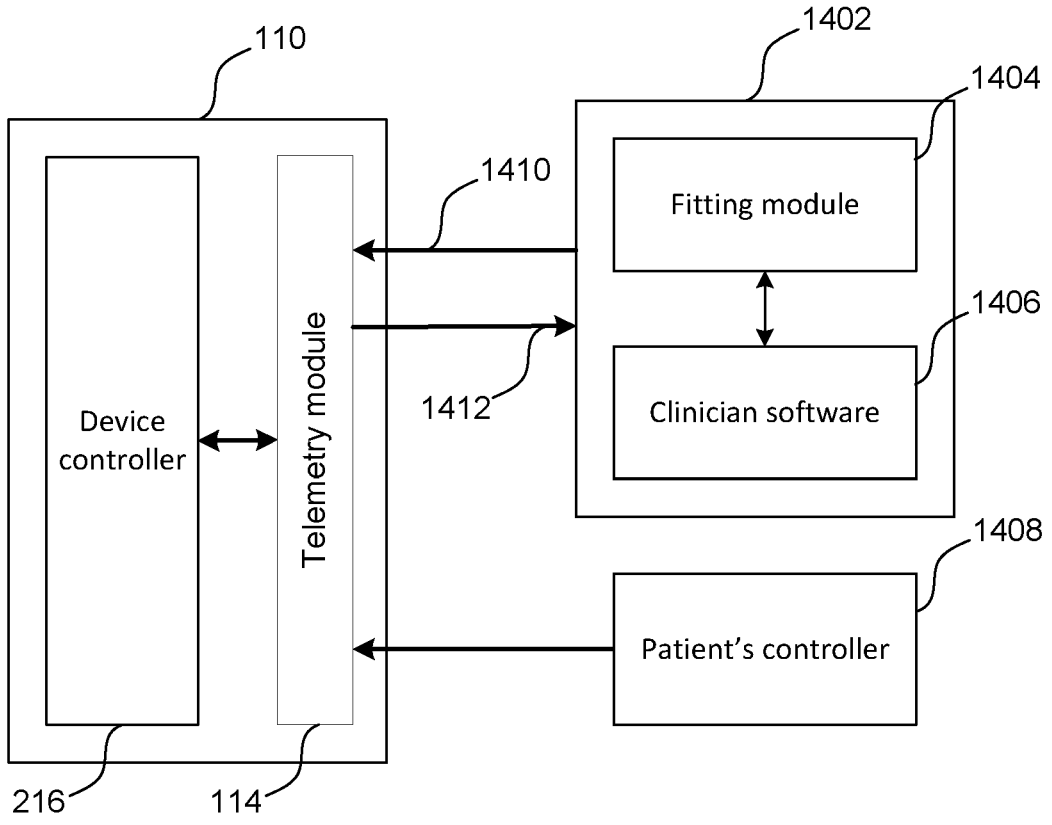
FIG. 14 shows a system comprising the implantable stimulation device of FIG. 2 in communication with modules that are not implanted in the patient, according to an embodiment.

FIG. 14—Configuration of the Stimulation Device

FIG. 14 shows a system comprising the implantable electronics module 110 of FIG. 2 in communication with modules that are not implanted in the patient, according to an embodiment. The electronics module 110 is in communication, via telemetry module 114 and communication means 1410, with configuration module 1402. Configuration module 1402 comprises a transmission port for transmitting information to the electronics module 110 via communication means 1410. The configuration module 1402 also comprises a reception port for receiving information from the electronics module 110 via communication means 1412.

The configuration module 1402 receives data from the electronics module 110 and provides configuration settings to the electronics module 110, during a configuration process. The configuration process may occur over a series of discrete configuration steps. Furthermore, the configuration process may be repeated, as needed, to ensure therapeutic operation of the electronics module 110.

Initial and Revised Target Recruitment Levels

As part of the configuration process, the configuration module 1402 communicates an initial target recruitment level to the device controller 216, via telemetry module 114. During operation of the implanted electronics module 110, the clinician software 1406 may communicate an indication of a revised target recruitment level to the device controller 216, via telemetry module 114. Similarly, the patient's controller 1408 may communicate an indication of a revised target recruitment level to the device controller 216. Upon receiving an indication of a revised target recruitment level, the device controller 216 revises the initial target recruitment level using the indication of the revised target recruitment level and configures the loop controller 310 to provide stimulus to achieve the revised target recruitment level. In one embodiment, the indication of a revised target recruitment level comprises an indication of whether to increase or decrease the current target recruitment level.

In the embodiment shown in FIG. 14, the configuration module 1402 comprises software executing on a computer device external to the patient. In another embodiment, the fitting module 1404 comprises firmware executing within the implantable electronics module 110, for example on the device controller 216. In another embodiment, the fitting module 1404 comprises both software components that are executed on processors external to the implantable electronics module 110, and firmware components that are executed on processors internal to the implantable electronics module 110.

Figure 15:
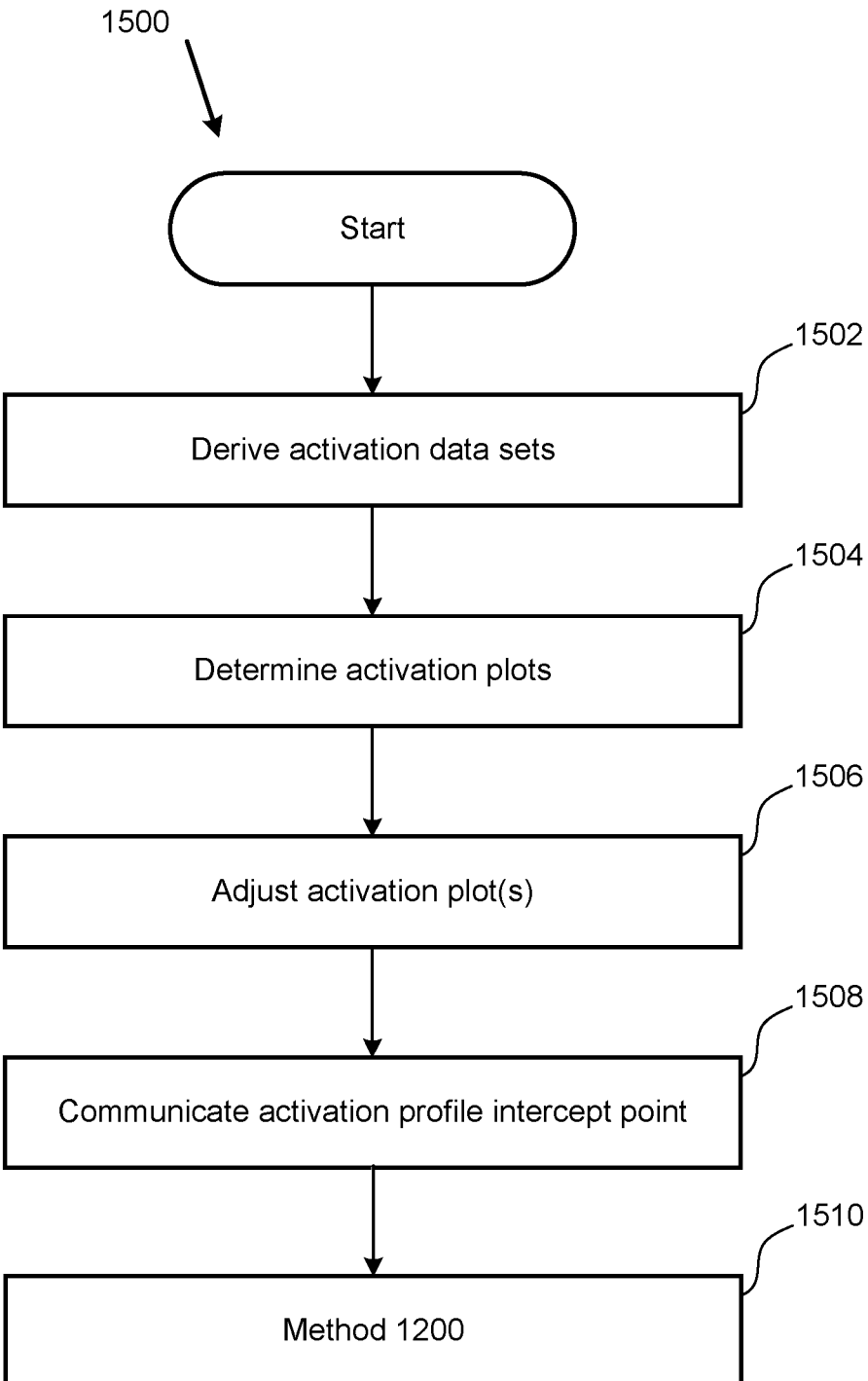
FIG. 15 illustrates a method of controlling a neural stimulus as described with reference to FIG. 14, according to an embodiment.

FIG. 15—Method of the System

FIG. 15 illustrates a method 1500 of controlling a neural stimulus as described with reference to FIG. 14, according to an embodiment. The neural stimulus is defined by at least one stimulus parameter. In one embodiment, steps 1502 to 1508 of method 1500 are performed by configuration module 1402, which is external to the electronics module 110. In other embodiments, some or all of steps 1502 to 1508 of method 1500 are performed by the electronics module 110.

In step 1502, the fitting module 1404 of the configuration module 1402 derives a plurality of activation data sets. In step 1504, the fitting module 1404 determines a plurality of activation plots for a patient, each activation plot being based on one of the plurality of activation data sets. Each activation data set, and therefore each activation plot, is associated with a unique posture of the patient. In step 1506, the fitting module 1404 adjusts at least one of the plurality of activation plots, such that all of the plurality of activation plots, when extrapolated, intersect at an activation plot intercept point. In step 1508, the configuration module 1402 communicates information indicative of the activation plot intercept point to the electronics module 110 via the telemetry module 114. The activation plot intercept point indicates an intercept point for a plurality of activation plots associated with the tissue. The electronics module 110 is electrically connected to the patient's tissue.

In step 1510, the electronics module 110 performs the steps of method 1200 to control the neural stimulus using the intercept point.

Figure 16:
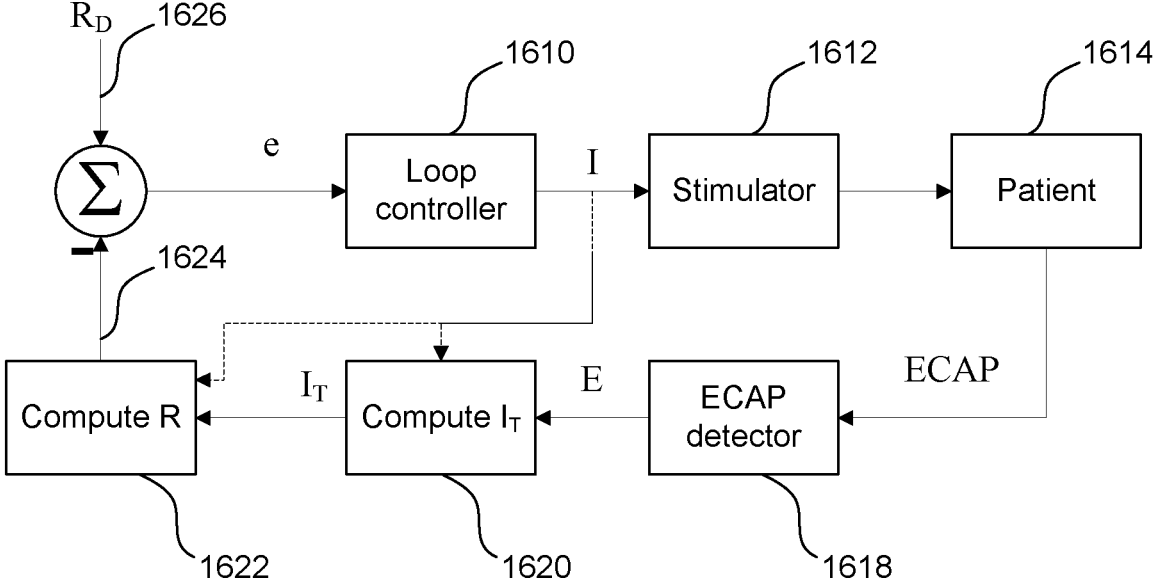
FIG. 16 is a system diagram illustrating a feedback loop of a stimulation device, according to an embodiment.

FIG. 16—Modified Feedback Loop

FIG. 16 is block diagram illustrating a variant of the feedback loop 300 of FIG. 3 for adjusting a stimulus intensity level of a neural stimulus applied to the patient 1614, according to one aspect of the present technology. The stimulator 1612 is similar to the stimulator 312, taking a stimulus intensity parameter I and converting it into a neural stimulus. The ECAP detector 1618 combines the functions of the amplifier 318 and the detector 320, providing a measure E of the amplitude of the evoked response (ECAP) of the patient. Computation module 1620 computes the threshold stimulus current $I_T$ from the amplitude E and the stimulus intensity parameter I. Computation module 1620 computes $I_T$ as an E-weighted average of I and $I_0$ as per Equation 3.

Computation module 1622 then computes an estimated recruitment level R 1624 from the stimulus intensity parameter/and the threshold stimulus current $I_T$ from computation module 1620. Computation module 1622 computes the estimated recruitment level R 1624 as the proportional excess of I over $I_T$ as per Equation 4. In one embodiment, computation modules 1620 and 1622 are combined into a single computation module that computes R 1624 directly from I and E by combining Equations 3 and 4:

$$R = \frac{E(I - I_0)}{E_0 I + I_0 E} \qquad \text{(Equation 8)}$$

Note, if $I_0 == 0$, Equation 8 reverts to $R = E/E_0$, i.e. R is proportional to E and independent of current. Thus, the recruitment-based feedback control of FIG. 16 degenerates to ECAP-based feedback control as in the feedback loop 300 of FIG. 3.

The loop controller 1610 is similar to the loop controller 310, calculating an adjusted value for stimulus intensity parameter I, based on the difference e between the estimated recruitment level R 1624 determined by computation step 1622 and desired (target) recruitment level $R_D$ 1626 with the aim of providing neural stimulus at an intensity that allows the patient 1614 to receive consistent comfortable and therapeutic stimulation.

Fitting Process

Once the implantable device is implanted within the patient, the device may undergo a fitting process so that the implantable device can be configured to provide therapeutic stimulation.

In one embodiment, the fitting process is performed by a fitting module 1404 which is in communication with the device controller 216 via telemetry module 114.

In step 1502, the fitting module 1404 derives activation data sets for a plurality of different postures of the patient. To obtain the activation data sets, the fitting module configures the implanted device to generate neural stimulus at a defined stimulus intensity level, and obtains the measured ECAP value that is evoked by that stimulus intensity level. The fitting module 1404 forms a data couple comprising the stimulus intensity level and the measured ECAP value. During the fitting process, the fitting module 1404 and implanted device repeat these steps for a number of stimulus intensity levels, thereby forming an activation data set comprising a plurality of data couples for each posture, and in a number of different patient postures to obtain the activation data sets.

In step 1504, the fitting module 1404 determines baseline activation plots for a patient based on the activation data sets obtained during step 1502 of the fitting process. The baseline activation plots may represent linear approximations to the empirically derived activation data sets.

Activation Plot Adjustment Module (APAM)

The fitting module 1404 comprises an activation plot adjustment module (APAM), configured to adjust one or more of the baseline activation plots. In step 1506, the APAM adjusts at least one of the baseline activation plots to ensure that the adjusted activation profile comprises activation plots that have a common intercept point.

In one embodiment, the fitting module 1404 performs steps 1504 and 1506 as a single step, such that the activation plots are determined from the activation data sets so that all the activation plots intersect at a common intercept point.

The adjusted activation profile can be represented by the adjusted activation profile information (AAPI), which provides a representation of the patient's expected ECAP response to a range of stimulus intensity levels, when the patient is in one or more different postures. In one embodiment, the AAPI comprises an indication of the Cartesian coordinates of the common intercept point. The AAPI may also comprise information indicative of the slopes of the activation plots.

In step 1508, the fitting module 1404 communicates the adjusted activation profile information (AAPI) to the loop controller 310. The loop controller 310 uses the AAPI, while performing method 1200, to adjust the stimulation intensity level, based on the measured ECAP response.

It will be appreciated by persons skilled in the art that numerous variations and/or modifications may be made to the above-described embodiments, without departing from the broad general scope of the present disclosure. Furthermore, it will be appreciated by persons skilled in the art that embodiments disclosed herein can be combined with one or more other embodiment disclosed herein, without departing from the broad general scope of the present disclosure. The present embodiments are, therefore, to be considered in all respects as illustrative and not restrictive.

References herein to software are to be understood as referring to executable instructions stored in volatile or non-volatile memory. References herein to estimation, determination, comparison and the like are to be understood as referring to an automated process carried out on data by a processor operating to execute a predefined procedure suitable to effect the described estimation, determination and/or comparison step(s). The approaches presented herein may be implemented in hardware (e.g. using digital signal processors, application specific integrated circuits (ASICS) or field programmable gate arrays (FGPAs)), or in software (e.g., using instructions tangibly stored on computer-readable media for causing a data processing system to perform the steps described herein), or in a combination of hardware and software. The invention can also be embodied as computer-readable code on a computer-readable medium. The computer-readable medium can include any data storage device that can store data which can thereafter be read by a computer system. Examples of the computer-readable medium include read-only memory (ROM), random-access memory (RAM), magnetic tape, optical data storage device, flash storage devices, or any other suitable storage devices. The computer-readable medium can also be distributed over network-coupled computer systems so that the computer readable code is stored and/or executed in a distributed fashion.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention claimed is:

1. A method of controlling a neural stimulus, the neural stimulus being defined by at least one stimulus parameter, the method comprising:

applying a neural stimulus to a neural tissue of a patient in accordance with a stimulus parameter, the stimulus parameter being at a first stimulus intensity level;

measuring a response of the neural tissue, the response being evoked by the neural stimulus;

determining a second stimulus intensity level, based on a predetermined activation plot intercept point that indicates an intersection point for a plurality of activation plots associated with the neural tissue, the first stimulus intensity level, the measured response of the neural tissue and a predetermined target recruitment level;

adjusting the stimulus parameter to the second stimulus intensity level; and applying a further neural stimulus to the neural tissue in accordance with the adjusted stimulus parameter.

2. The method of claim 1, further comprising determining a threshold stimulus intensity level, based on the activation plot intercept point, the first stimulus intensity level and the measured response of the neural tissue, wherein determining the second stimulus intensity level comprises determining the second stimulus intensity level based on the threshold stimulus intensity level and the target recruitment level.

3. The method of claim 2, wherein determining the second stimulus intensity level comprises determining a multiplication of the threshold stimulus intensity level and the target recruitment level plus one.

4. The method of claim 2, wherein the activation plot intercept point comprises an intercept stimulus intensity term and an intercept evoked response term.

5. The method of claim 4, wherein the intercept stimulus intensity term is a positive non-zero value.

6. The method of claim 1, wherein determining the second stimulus intensity level comprises calculating an estimated recruitment level, and determining a difference between the estimated recruitment level and the target recruitment level.

7. The method of claim 1, further comprising receiving configuration information indicative of the activation plot intercept point.

8. The method of claim 1, further comprising receiving configuration information indicative of the target recruitment level.

9. The method of claim 1, wherein each activation plot is indicative of a relationship between evoked responses of the neural tissue and a plurality of stimulus intensity levels, for one of a plurality of different postures of the patient.

10. The method of claim 1, wherein each activation plot of the plurality of activation plots is indicative of a relationship between the at least one stimulus parameter and an evoked response of the neural tissue, wherein each relationship comprises a monotonically increasing linear section, and the monotonically increasing linear section can be extrapolated on a Cartesian plane to produce an extrapolated linear section, and wherein the extrapolated linear section of each activation plot of the plurality of activation plots passes through the activation plot intercept point.

11. The method of claim 4, wherein determining the threshold stimulus intensity level comprises:

determining a first term to be equal to the intercept evoked response term multiplied by the first stimulus intensity level;

determining a second term to be equal to the intercept stimulus intensity term multiplied by the measured response of the neural tissue;

determining a third term to be equal to the measured response of the neural tissue added to the intercept evoked response term;

determining a fourth term to be equal to the first term added to the second term; and determining the threshold stimulus intensity level to be equal to the fourth term divided by the third term.

12. An implantable device for controllably generating a neural stimulus, the neural stimulus being defined by at least one stimulus parameter, the device comprising:

a stimulator configured to apply a neural stimulus to a neural tissue of a patient, in accordance with the at least one stimulus parameter;

measurement circuitry for measuring an evoked response of the neural tissue;

a communication port for receiving information from a data source; and a controller configured to:

control the stimulator to apply the neural stimulus, in accordance with a stimulus parameter, the stimulus parameter being at a first stimulus intensity level;

measure a response of the neural tissue, the response being evoked by the neural stimulus;

determine a second stimulus intensity level, based on a predetermined activation plot intercept point that indicates an intersection point for a plurality of activation plots associated with the neural tissue, the first stimulus intensity level, the measured response of the neural tissue and a predetermined target recruitment level;

adjust the at least one stimulus parameter to the second stimulus intensity level; and control the stimulator to apply a further neural stimulus to the neural tissue in accordance with the adjusted stimulus parameter.

13. The device of claim 12, further comprising firmware for configuring the controller.

14. A system for controlling a neural stimulus for application to a neural tissue of a patient, the neural stimulus being defined by at least one stimulus parameter, the system comprising a configuration module and an implantable device configured to be in electrical communication with the neural tissue, the configuration module comprising a transmission port for transmitting information indicative of an activation plot intercept point to the implantable device, the activation plot intercept point indicating an intersection point for a plurality of activation plots associated with the neural tissue; and the implantable device comprising:

a stimulator configured to apply the neural stimulus to a neural tissue of a patient in accordance with the at least one stimulus parameter;

measurement circuitry for measuring an evoked response of the neural tissue;

a reception port for receiving the information from the configuration module; and a controller configured to:

control the stimulator to apply the neural stimulus to a neural tissue of a patient, in accordance with a stimulus parameter, the stimulus parameter being at a first stimulus intensity level;

measure a response of the neural tissue, the response being evoked by the neural stimulus;

determine a second stimulus intensity level, based on the activation plot intercept point, the first stimulus intensity level, the measured response of the neural tissue and a predetermined target recruitment level;

adjust the stimulus parameter to the second stimulus intensity level; and control the stimulator to apply a further neural stimulus to the neural tissue in accordance with the adjusted stimulus parameter.

15. The system of claim 14, further comprising a fitting module for determining the activation plot intercept point, the fitting module comprising instructions which, when executed by one or more processors, causes performance of the following:

determining a plurality of activation plots, each activation plot based on one of a plurality of activation data sets;

adjusting at least one of the plurality of activation plots, such that all of the plurality of activation plots, when extrapolated, intercept at an activation plot intercept point; and communicating information indicative of the activation plot intercept point to the implantable device.

* * * * *